(12) United States Patent
Nordstrom et al.

(10) Patent No.: US 9,883,794 B1
(45) Date of Patent: Feb. 6, 2018

(54) METHOD AND APPARATUS FOR TESTING FOR COLOR VISION LOSS

(71) Applicants: Cheryl Nordstrom, Hinsdale, IL (US); Jeffrey Rabin, San Antonio, TX (US); John M. Gooch, Dayton, OH (US)

(72) Inventors: Cheryl Nordstrom, Hinsdale, IL (US); Jeffrey Rabin, San Antonio, TX (US); John M. Gooch, Dayton, OH (US)

(73) Assignee: Innova Systems, Inc., Burr Ridge, IL (US)

( * ) Notice: Subject to any disclaimer, the term of this patent is extended or adjusted under 35 U.S.C. 154(b) by 86 days.

(21) Appl. No.: 14/819,046

(22) Filed: Aug. 5, 2015

Related U.S. Application Data

(63) Continuation of application No. 14/251,286, filed on Apr. 11, 2014, now abandoned, which is a (Continued)

(51) Int. Cl.
  *A61B 3/02* (2006.01)
  *A61B 3/06* (2006.01)
  *A61B 3/00* (2006.01)

(52) U.S. Cl.
  CPC ............ *A61B 3/066* (2013.01); *A61B 3/0025* (2013.01); *A61B 3/0041* (2013.01); *A61B 3/022* (2013.01)

(58) Field of Classification Search
  CPC ....... A62B 3/066; A62B 3/022; A62B 3/0025; A62B 3/00241
  (Continued)

(56) References Cited

U.S. PATENT DOCUMENTS

2010/0188639 A1* 7/2010 Carda .................... A61B 3/066
  351/242

OTHER PUBLICATIONS

Jeff Rabin, John Gooch, and Douglas Ivan. Rapid Quantification of Color Vision: The Cone Contrast Test. Investigative Ophthalmology & Visual Science, Feb. 2011, vol. 52, No. 2 816 Copyright 2011 The Association for Research in Vision and Ophthalmology, Inc.*

(Continued)

*Primary Examiner* — Bumsuk Won
*Assistant Examiner* — Collin X Beatty
(74) *Attorney, Agent, or Firm* — Simpson & Simpson, PLLC

(57) ABSTRACT

A method and apparatus for administering eye tests to identify cone sensitivity loss associated with hereditary and acquired color vision loss which may be used for early detection, progress, treatment, and monitoring of eye conditions, traumatic brain injury, optic neuritis, systemic and neurological diseases including Glaucoma, Retinopathy, Age-Related Macular Degeneration, Multiple Sclerosis, Alzheimer's Disease, and Parkinson's Disease and retinal toxicity. Particularly, the method and apparatus disclosed uses a Cone Contrast Test (CCT) to test individuals for hereditary or acquired color vision loss associated with (a) early signs of potential disease/damage/toxicity in an effort to (i) provide opportunity for treatment, and (ii) prevent permanent eye damage, and (b) monitor progress and treatment of such disease/damage/toxicity. The system comprises a computer system including an input device and a display device, and the accuracy and repeatability of the testing is provided by repeated calibration using a colorimeter.

27 Claims, 34 Drawing Sheets

Related U.S. Application Data continuation of application No. 13/887,272, filed on May 3, 2013, now abandoned.

(60) Provisional application No. 61/642,378, filed on May 3, 2012, provisional application No. 61/642,292, filed on May 3, 2012.

(58) Field of Classification Search
USPC .......................................... 351/239, 242, 246
See application file for complete search history.

(56) References Cited

OTHER PUBLICATIONS

Rabin, Jeff, et al. "Rapid Quantification of Color Vision: The Cone Contrast Test," Investigative Ophthalmology & Visual Science; Feb. 2011, vol. 52, No. 2, pp. 816-820.

Rabin, Jeff. "Quantification of Color Vision with Cone Contrast Sensitivity," Visual Neuroscience, Cambridge University Press, 2004, 21, pp. 483-485.

Rabin, Jeff. "Cone-Specific Measures of Human Color Vision," Visual Sciences Branch, Aircrew Health and Performance Division, US Army Aeromedical Research Laboratory, Fort Rucker, Alabama, Jul. 23, 1996, (Dec. 1996) vol. 37, No. 13, pp. 2771-2774.

http://spyder.datacolor.com/products; SPYDER 3tm sold by Datacolor of Lawrenceville, NJ, last accessed Apr. 10, 2017.

\* cited by examiner

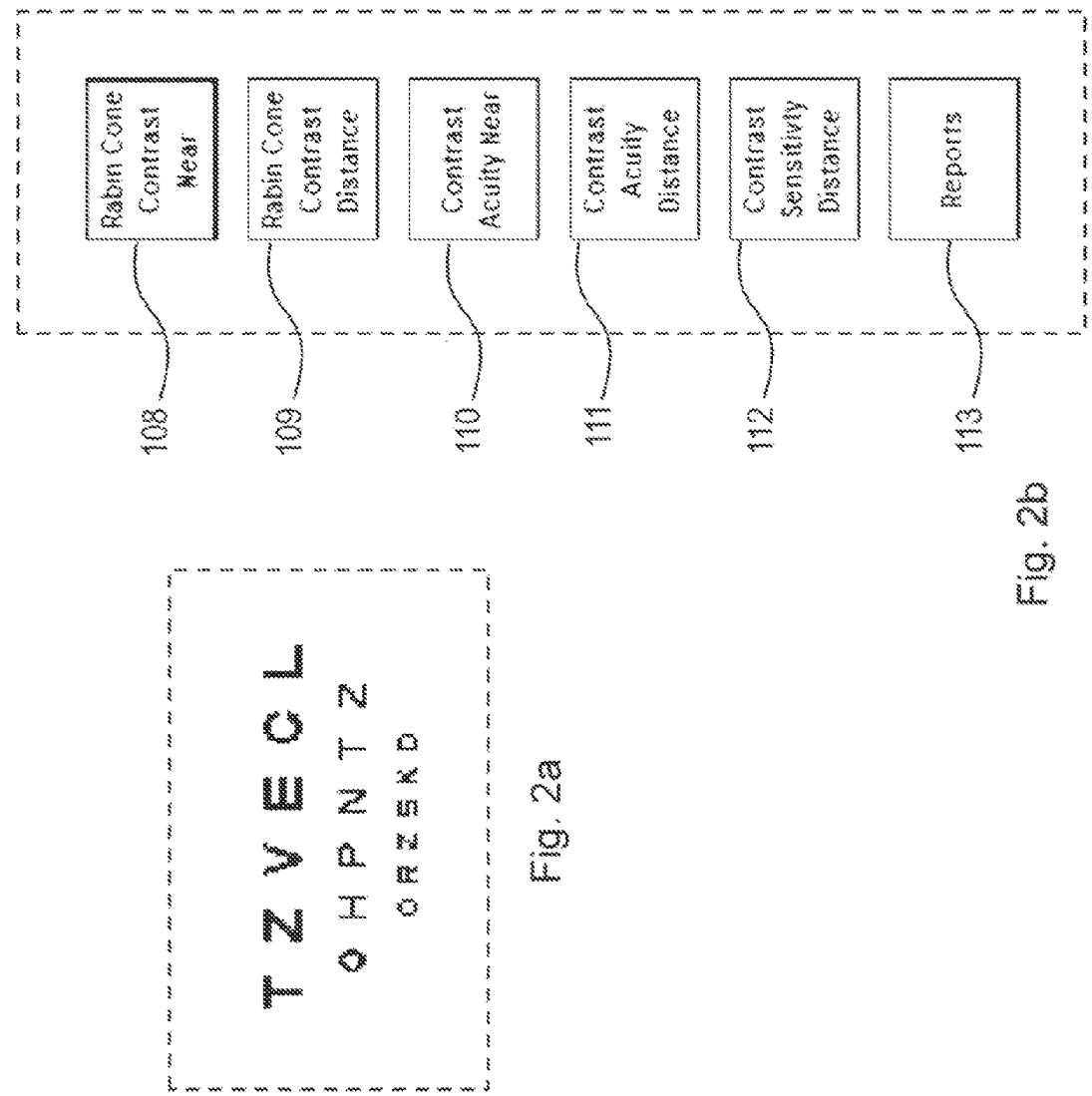

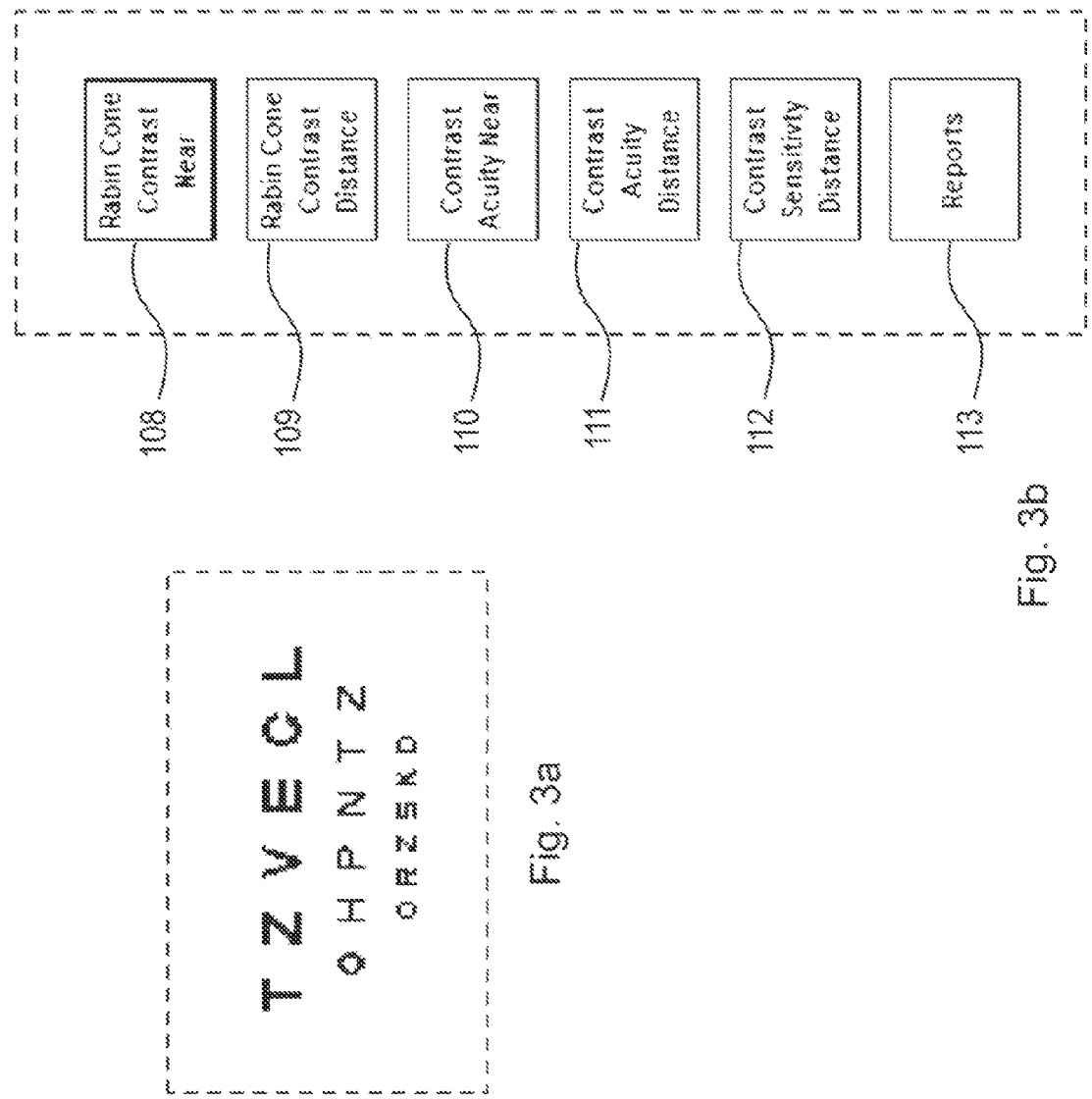

METHOD AND APPARATUS FOR TESTING FOR COLOR VISION LOSS

CROSS-REFERENCE TO RELATED APPLICATIONS

This patent application is filed under 35 U.S.C. § 111(a) and § 120 and is a continuation of U.S. Nonprovisional patent application Ser. No. 14/251,286, filed Apr. 11, 2014, which is a continuation of U.S. Nonprovisional patent application Ser. No. 13/887,272, filed May 3, 2013, which claims the benefit under 35 U.S.C. § 119(e) of U.S. Provisional Patent Application No. 61/642,378, filed May 3, 2012 and U.S. Provisional Patent Application No. 61/642,292, filed May 3, 2012 which applications are incorporated herein by reference.

STATEMENT REGARDING FEDERALLY SPONSORED RESEARCH OR DEVELOPMENT

This invention was made with government support under USAF CRADA NUMBER 10-048-SM-01CRD and USAF CRADA NUMBER 10-048-SM-01CRD Modification Number 1 awarded by the Department of the Air Force. The Government has certain rights to use the invention.

REFERENCE TO COMPUTER PROGRAM LISTING APPENDIX

The present application includes the following computer program listing appendix. The computer program listing appendix is expressly incorporated herein by reference in its entirety. The appendix contains an ASCII text file of the computer program as follows:

| File | Size | Date |
|---|---|---|
| AdminWindow.txt | 15.6 KB | Created May 3, 2013 |
| AdminWindow-2.txt | 8.93 KB | Created May 3, 2013 |
| app.txt | .5 KB | Created May 3, 2013 |
| appmanifest.txt | 2.44 KB | Created May 3, 2013 |
| Browser.txt | 2.63 KB | Created May 3, 2013 |
| Browser-2.txt | 2.79 KB | Created May 3, 2013 |
| FileIO.txt | 1.29 KB | Created May 3, 2013 |
| HtmlReport.txt | 108 KB | Created May 3, 2013 |
| IniBS.txt | 1.62 KB | Created May 3, 2013 |
| LogInWindow.txt | 2.78 KB | Created May 3, 2013 |
| LogInWindow-2.txt | 3.38 KB | Created May 3, 2013 |
| MainWindow.txt | 70.7 KB | Created May 3, 2013 |
| MainWindow-2.txt | 26.9 KB | Created May 3, 2013 |
| mod1.txt | 294 KB | Created May 3, 2013 |
| mod3.txt | 175 KB | Created May 3, 2013 |
| mod4.txt | 67.5 KB | Created May 3, 2013 |
| PatientsWindow.txt | 13.0 KB | Created May 3, 2013 |
| colortest.txt | 38.5 KB | Created May 3, 2013 |
| form1.txt | 24.4 KB | Created May 3, 2013 |

FIELD OF THE INVENTION

The present method and apparatus relate to eye tests for hereditary and acquired color vision loss and may be used for the early detection, progress, treatment and monitoring of eye conditions, optic neuritis, traumatic brain injury, systemic and neurological diseases including Glaucoma, Retinopathy, Age-Related Macular Degeneration, Multiple Sclerosis, potentially Alzheimer's Disease and Parkinson's Disease, as well as Retinal Toxicity due to high-risk medications. Particularly, the systems and methods disclosed herein use a Cone Contrast Test (CCT) to identify hereditary color deficiency and acquired color vision loss associated with early disease/damage/toxicity to (a) alert for early disease/damage/toxicity in an effort to (i) provide opportunity for treatment, and (ii) prevent permanent eye damage, and (b) monitor progress and treatment of such disease/damage/toxicity.

BACKGROUND OF THE INVENTION

The human eye sees color as a result of three types of receptors, called cones, listed in the chart below. A range of wavelengths of light stimulates each of these receptor types to varying degrees. Yellowish-green light, for example, stimulates both L and M cones equally strongly, but only stimulates S-cones weakly; red light stimulates L cones much more than M cones, and S cones hardly at all; blue-green light stimulates M cones more than L cones, and S cones a bit more strongly; and blue light stimulates S cones more strongly than red or green light, but L and M cones more weakly. The brain combines the information from each type of receptor to give rise to different perceptions (i.e., colors) of different wavelengths of light.

| Cone type | Name | Range | Peak wavelength |
|---|---|---|---|
| S | B | 400-500 nm | 420-440 nm |
| M | Γ | 450-630 nm | 534-555 nm |
| L | P | 500-700 nm | 564-580 nm |

Test procedures such as optical computed tomography (OCT), visual field analyzers, etc., are used primarily to screen and diagnose specific eye disease. OCTs and visual field analyzers are tests generally used once the patient is symptomatic, well after permanent eye damage has occurred.

A test, called the Cone Contrast Test (CCT), is used to determine deficiencies of these cones in an individual's eye. The CCT is explained in greater detail in the published articles titled "Rapid Quantification of Color Vision: The Cone Contrast Test" by Rabin et al. published in *Investigative Ophthalmology & Visual Science*, February 2011, Vol. 52, No. 2, and "Quantification of Color Vision with Cone Contrast Sensitivity" by Jeff Rabin (2004), 21, pp. 483-485, the disclosures of which are hereby incorporated by reference.

The CCT is a functional test, making it a broad, non-disease-specific test. These features make CCT an affordable screening tool able to detect cone sensitivity degradation associated with a broad spectrum of disease/toxicity early enough to, with treatment, potentially prevent permanent eye damage. The CCT may also be used as a predictive test for eye systemic, and neurological disease and retinal toxicity, as well as a monitoring test for disease/toxicity progression and treatment.

Consistent calibration of a color display monitor for administering the CCT is needed. Additionally, a low cost calibration system is needed due to inconsistent calibration over time. With standard "off-the-shelf" colorimeters, interference from other software, including software produced by Microsoft Corporation, override calibration values and render the test invalid.

SUMMARY OF THE INVENTION

The invention broadly comprises a computerized method for administering a cone contrast (CCT) color vision test to a patient, comprising the steps of (a) displaying a first character in a first color at a first contrast level on a display driven by the computer; (b) receiving a first input signal from the patient via an input device connected to the computer, where the input signal is indicative of whether the patient recognizes the first character displayed in the first color at the first contrast level; (c) displaying a second character in the first color at a second contrast level on the display driven by the computer; (d) receiving a second input signal from the patient via an input device connected to the computer, where the input signal is indicative of whether the patient recognizes the second character displayed in the first color at the second contrast level; (e) assigning a score to the first and second input signals, the score related to sensitivity of a cone in the patient's eye to the first color at the first and second contrast levels; and, (f) storing the score in a storage device to track the cone sensitivity over time.

The invention also broadly comprises an apparatus for administering a cone contrast (CCT) color vision test to a patient, comprising (a) a general purpose computer specially programmed for displaying a first character in a first color at a first contrast level on a display driven by the computer; (b) means for receiving a first input signal from the patient via an input device connected to the computer, where the input signal is indicative of whether the patient recognizes the first character displayed in the first color at the first contrast level; (c) means for displaying a second character in the first color at a second contrast level on the display driven by the computer; (d) means for receiving a second input signal from the patient via an input device connected to the computer, where the input signal is indicative of whether the patient recognizes the second character displayed in the first color at the second contrast level; (e) means for assigning a score to the first and second input signals, the score related to sensitivity of a cone in the patient's eye to the first color at the first and second contrast levels; and, (f) means for storing the score in a storage device in communication with the computer to track the cone sensitivity over time.

While this invention is susceptible of embodiments in many different forms, there is shown in the drawings and will herein be described in detail a preferred embodiment of the invention with the understanding that the present disclosure is to be considered as an exemplification of the principles of the invention and is not intended to limit the broad aspect of the invention to embodiments illustrated.

The invention comprises a method and apparatus for screening and monitoring progress and treatment of systemic and neurological eye diseases. The method and apparatus include a Cone Contrast Test (CCT) which measures and scores color perception by cone type and assigns a score by cone type. The method and apparatus further include a comparison of such scores to a base line. Using CCT for the screening of potential disease/toxicity is an efficient, fast and low-cost procedure.

The apparatus comprises a computer, including input device and display device, for administering the CCT to individuals and, based on the test results and other factors, determining the early and late stages of one of Glaucoma, Retinopathy, Age-Related Macular Degeneration, Multiple Sclerosis, potentially Alzheimer's Disease and Parkinson's Disease, as well as Retinal Toxicity due to high-risk medications, as disclosed in the Appendices. The method is implemented by the apparatus.

The Cone Contrast Test presents random colored characters (for example, letters, numbers or symbols) to excite the red, green and blue cones in decreasing contrast sensitivity levels to identify the patients' Cone Contrast threshold and score for each cone type in each eye. The target is presented at a size well above a "normal" 20/20 acuity level so that the patient's cone contrast score is not affected by a limited acuity ability.

Upon each character presentation, the patient selects the corresponding character (for example, a letter, number or symbol) he sees from a response table or grid. If he does not see the character presentation, he may select "Pass".

The patient interface consists of a computer mouse that may be used at a desk or in an exam room at a distance. Future patient interfaces may include a response keypad, notebook, tablet computer, touch screen, or voice recognition.

The Cone Contrast Test is fully automated, presenting each character for a specific, limited duration. Limiting the presentation time prevents a color deficient patient from potentially perceiving visual clues to aid him in his response and potentially affecting his score.

Further, elderly patients may not be familiar with computers, and thus may not be as responsive even though they are not color deficient. A "blanking period" option may be selected for patients requiring more time with the response unit. Specifically, after the character is presented for a fixed duration, the target letter is removed from the screen. The "blanking period" allows older patients, as well as patients with physical or cognitive limitations enough time to respond without introducing visual clues that could potentially alter their actual threshold and score.

Alternatively, an Orientation Screen, presented prior to the test for each eye, may detect the actual response time for the individual patient and adjust the presentation time for each target letter/number to achieve a Patient-Specific Presentation Time that would accommodate the need for additional response time due to computer, physical or cognitive limitations of each individual patient.

The blanking option or patient-specific presentation time is a key component for the Early Eye Disease Detection and Monitoring component of the Cone Contrast Test, as the majority of patients developing eye disease are elderly and may need extra time to respond due to unfamiliarity with a computer mouse or physical or cognitive limitations.

A staircase method is used to present color contrast levels by cone type, allowing the test to be administered more quickly. The contrast presentations are reduced by two levels at a time if the patient correctly identifies the character at that contrast level. The contrast level is increased if two or more characters within a contrast level are incorrectly identified.

The colors presented are precisely selected to excite only one cone type at a time, allowing each cone type to be measured and scored independently. Color calibration and contrast calibration are critical to the validity of the test results.

The equipment is calibrated for both color and contrast. The color presentation must be accurate so that each cone type is tested individually (i.e., only one cone type responds). In turn, the accuracy of the contrast levels is equally important to determine threshold level.

The current system includes software that does not allow other software to change color or contrast calibration settings, to achieve a reliable computerized color vision test using a low-cost colorimeter.

The disclosed system utilizes display calibrating colorimeter hardware, such as SPYDER 3™ and related versions, manufactured and sold by DATACOLOR of Lawrenceville, N.J.

Since the CCT begins with establishing a baseline for each cone type for an individual and looks for degradation of the individual's color perception through repeated testing over time, calibration for repeatability is critical. Computer equipment and colorimeters can be changed, drift or fail over time, allowing color and contrast values to become out of calibration. To ensure that equipment stays within calibration and test results remain valid, the software forces an automatic in-field periodic calibration check. The CCT is self-calibrating, requiring the user only to position the photometer on the monitor and start the calibration. The calibration verification is done automatically and checks calibration values to original calibration values done at initial manufacturing. If the calibration is outside of tolerance, the system forces a complete calibration. If the calibration is still outside of tolerance, the system will alert the user and disable the use of the Cone Contrast Test until calibration can be completed within tolerance.

The duration between each calibration is established during set-up and may be adjusted based on clinic testing policy and procedure. The calibration time frame is pre-set for every seven days, but may be set according to individual testing policy and preference. Preferably, calibration automatically occurs at a predetermined interval of time. The automation alleviates the fear by some that the calibration may be skipped and test results may be rendered invalid.

Automated calibration verification enables a user of the invention to check for failing/failed hardware, including colorimeter, monitor, or computer changes to ensure valid test scores. The calibration verification of the present system is preferably set at a seven (7) day interval, requiring calibration be checked against the original calibration settings. Any significant change from original calibration settings requires a full calibration. If a full calibration is still outside of tolerances, the Cone Contrast Test is disabled until a calibration can be completed within tolerance. Replacing equipment, such as a photometer, monitor or CPU, may be required to achieve a valid calibration.

Since the equipment may be used for both screening and monitoring of disease/toxicity, the equipment has both a screening mode and a comprehensive testing mode to allow for Medicare or other insurance billing, with the comprehensive mode providing more thorough examination and reporting. A doctor specifies the mode based on the use of the instrument for the specific exam before conducting the test.

Variations in the testing method may include, but are not limited to (1) altering distance between screen and individual (e.g., 3, 4 or 6 meters), (2) a user interface such as voice recognition commands, wireless keyboard or other wired or wireless input devices, (3) blanking period or patient-specific response time, and (4) screening and testing modes.

Each test is scored by cone type and any cone deficiency is determined by comparing the patient's scores over time. Accuracy of CCT is very high in detecting Red, Green and Blue cone deficiencies. Deficiencies which present over time are predictive of early eye, systemic and neurological disease as well as retinal toxicity, whereas such deficiencies may otherwise be overlooked as anomalies.

Storing of cone contrast sensitivity scores and reporting data in a way that shows cone contrast sensitivity changes over time allows for potential disease/toxicity alerts. Reports show a change in cone contrast sensitivity by patient, per eye, by cone type and display an alert when the cone contrast sensitivity change is statistically significant. The reports can be viewed or printed to alert doctors and patients of potential disease or toxicity that should be further investigated.

Currently, significant change is thought to be the normal distribution of color normal patients score, >15 points. Further research may show that changes less than 15 points may also be significant to a specific patient baseline.

This type of tracking and reporting mechanism has never before been available, limiting prior art systems and methods to hereditary color deficiency scoring use or research where time permits for manual comparison. The disclosed system and method is the first CCT usable as an early eye, systemic and neurological disease and retinal toxicity detection system in a clinic setting, where time with the patient is limited. Comparison data and alerts are critical to interpret test results in the time frame required in a clinical setting.

Patient reports are stored on the computer hard drive and may be uploaded to electronic medical records.

As previously discussed, patient response time is captured and recorded for each cone type for every Cone Contrast Test. Mean response time by cone type, and by eye, is calculated and reported. Response times have been shown to correlate closely with cone deficiency, with color normal patients responding consistently within two seconds and color deficient patients responding much slower. Cone Contrast Sensitivity Response Time may serve as a new sensitive metric of color deficiency and early indicator of eye, systemic or neurological disease.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution.

BRIEF DESCRIPTION OF THE DRAWINGS

Various embodiments are disclosed, by way of example only, with reference to the accompanying drawings in which corresponding reference symbols indicate corresponding parts, in which:

FIG. 2a is an enlarged view of the enclosed region 2a shown in FIG. 2;
FIG. 2b is an enlarged view of the enclosed region 2b shown in FIG. 2;
FIG. 3a is an enlarged view of the enclosed region 3a shown in FIG. 3;
FIG. 3b is an enlarged view of the enclosed region 3b shown in FIG. 3.

DETAILED DESCRIPTION

At the outset, it should be appreciated that like drawing numbers on different drawing views identify identical, or functionally similar, structural elements of the embodiments set forth herein. Furthermore, it is understood that these embodiments are not limited to the particular methodology, materials and modifications described and as such may, of course, vary. It is also understood that the terminology used herein is for the purpose of describing particular aspects only, and is not intended to limit the scope of the disclosed embodiments, which are limited only by the appended claims.

Unless defined otherwise, all technical and scientific terms used herein have the same meaning as commonly understood to one of ordinary skill in the art to which these embodiments belong.

Moreover, although any methods, devices or materials similar or equivalent to those described herein can be used in the practice or testing of these embodiments, some embodiments of methods, devices, and materials are now described.

As discussed above, a cone contrast test presents characters with colors specific to each cone type in decreasing contrast steps down to or near the patient's cone contrast threshold. It tests all three color values—red, green and blue—in both right and left eyes. Characters or optotypes are presented at 20/300 (red, green) and 20/400 (blue) to avoid acuity function interference. The CCT presents 5 contrast levels in increments of two contrast levels or jumps until the patient responds incorrectly. At that time, the contrast level presentations begin at the next higher contrast level and proceeds in a sequential fashion through the duration of the test. The patient's cone score is determined based on the number of correct responses at each level.

Figure 1:
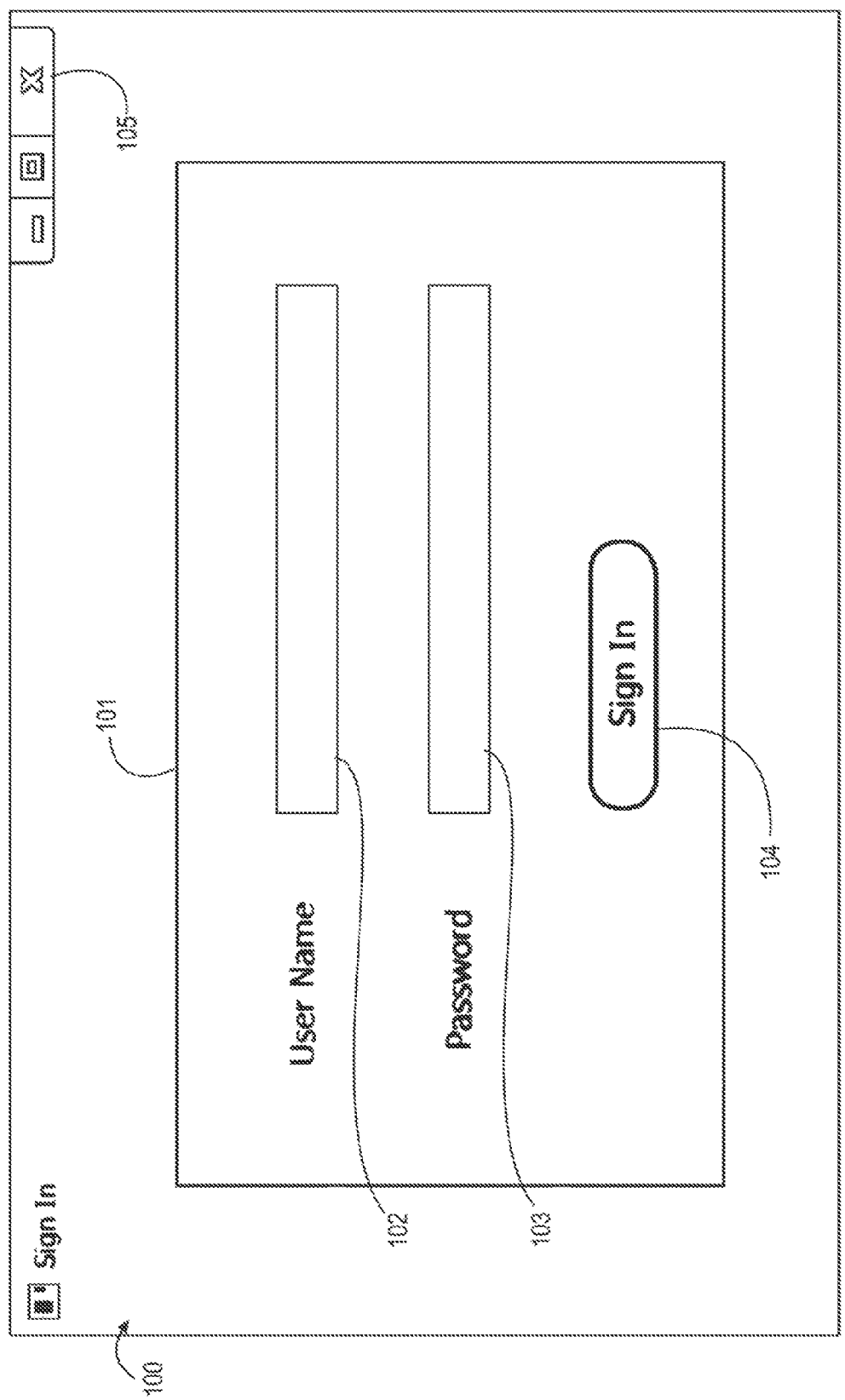
FIG. 1 is a screen shot of the invention.

Adverting now to the Figures, the following Figures show screenshots of testing software 100. FIG. 1 shows sign in screen 101 driven by a computer. Sign in screen 101 comprises user name field 102, password field 103, and sign in button 104. Upon commencing testing software 100, sign in screen 101 appears. In order to access testing software 100, a patient taking a CCT or an administrator directing the CCT, must input a user name and a password into user name field 102 and password field 103, respectively. A user can exit testing software 100 by selecting exit button 105 located at the top right of sign in screen 101.

Figure 2:
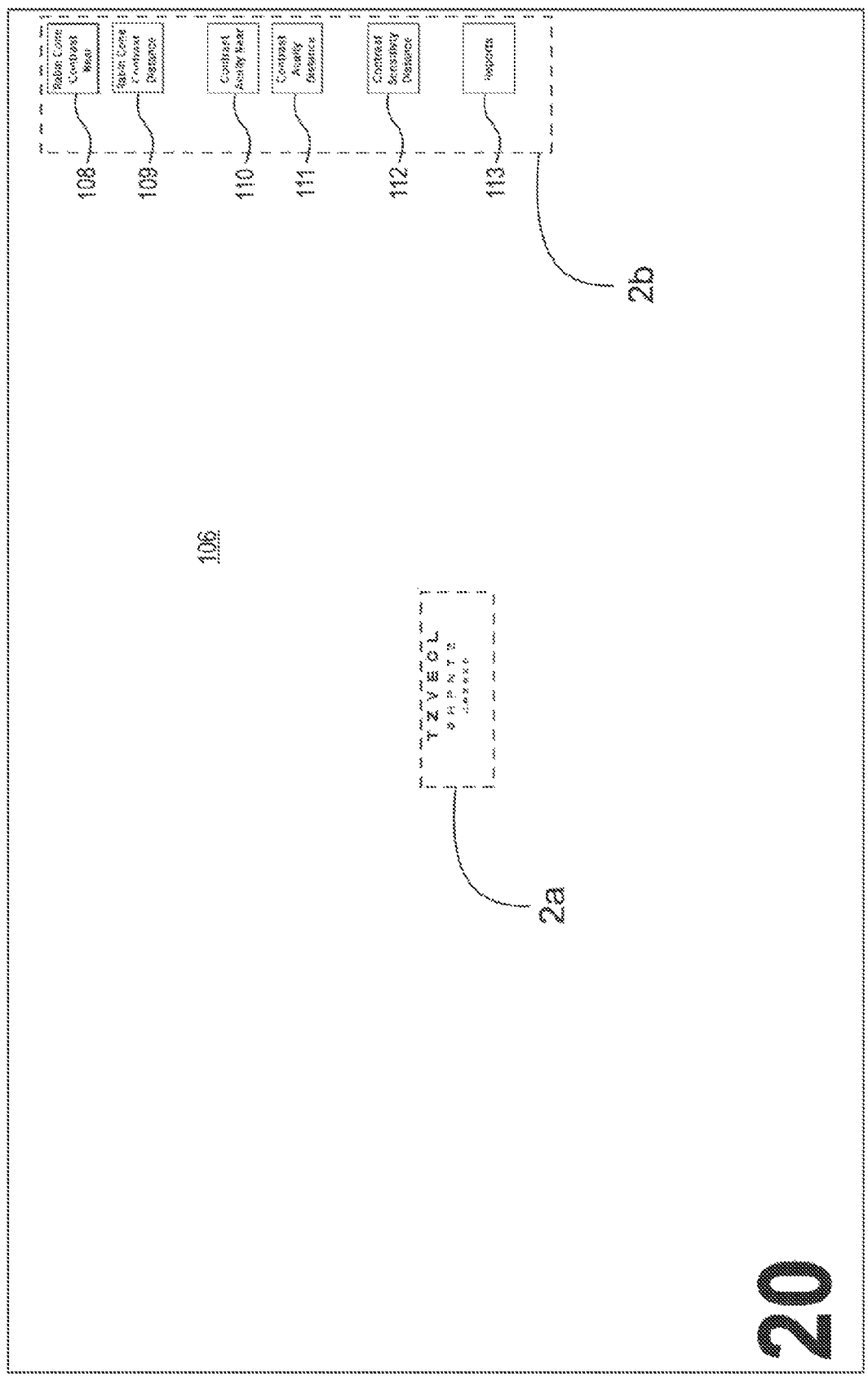
FIG. 2 is a screen shot of the invention.

Once sign in button 104 is selected, presentation option screen 106 of testing software 100 appears as shown in FIG. 2. Presentation option screen 106 comprises CCT near button 108, CCT distance button 109, contrast acuity near button 110, contrast acuity distance button 111, contrast sensitivity distance button 112, and reports button 113. The CCT may be conducted while a patient is seated at a desk with the computer displaying the CCT mounted thereon. In this case, a patient can use a computer mouse or some other means to select buttons in testing software 100 to be described in more detail below. Alternatively, the CCT may be conducted while a patient is seated or standing a distance from the computer displaying the CCT. In this case, an administrator directing or overseeing the CCT can operate a mouse connected to the computer displaying the CCT or some other interface may be involved to input a patient's responses. For example, voice recognition software could be used to transmit a patient's selections in or responses to the CCT, or a wireless mouse could be used. Regardless of the method used, acuity and cone contrast tests can be administered with a patient arranged proximate the display screen and at a distance away from the display screen. For near testing, a patient should be 18-24 inches from the display. For tests administered at a distance, a patient should be at least 9 feet from the display. If CCT near button 108 or contrast acuity near button 110 is selected, testing software 100 is directed to use characters at a default size based on the calibration of testing software 100. If CCT distance button 109 is selected, testing software 100 is directed to display higher quality characters, down to 20/10, during the CCT depending on the patient's distance from the computer display. Selecting CCT distance button 109 will cause testing software 100 to produce a distance field and the patient's distance from the computer display will need to be inputted into the distance field and transmitted to testing software 100 so the proper quality characters are used. For best results, the patient should be parallel to the display. Selecting contrast acuity distance button 111 or contrast sensitivity distance button 112 will similarly direct testing software 100 to use higher quality characters, down to 20/10, during the acuity or sensitivity tests depending on the patient's distance from the computer display. Reports button 113 will be discussed in more detail below. FIGS. 2a and 2b represent enlarged enclosed areas 2a and 2b, respectively, shown in FIG. 2.

The CCT should be conducted in dim room lighting. No light should be directed at the CCT display. However, some lighting is acceptable and will not interfere with the test.

Figure 3:
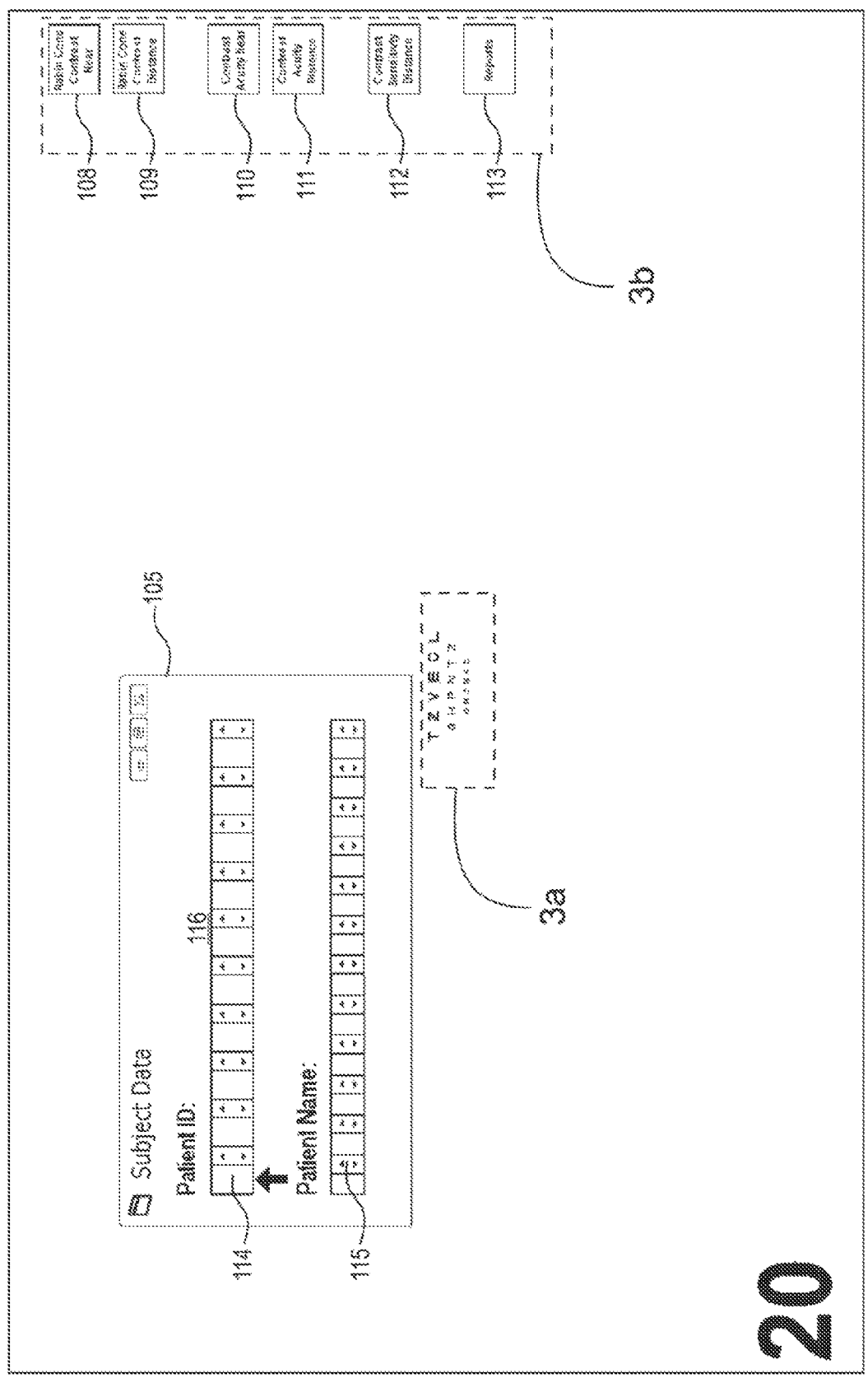
FIG. 3 is a screen shot of the invention.

Selection of the type of test desired (CCT near button 108, CCT distance button 109, contrast acuity near button 110, contrast acuity distance button 111, or contrast sensitivity distance button 112) will direct testing software 100 to produce subject data screen 116. Subject data screen 116 comprises patient ID field 114 and patient name field 115 shown in FIG. 3. Patient ID field 114 of testing software 100 is arranged to receive a 1-10 digit number identifying a patient. The number can but input using a keyboard, for example. Left and right arrows on a keyboard allow a user to move between digit entry fields. A patient's name, for example, John Doe is inputted into patient name field 115 using a keyboard, for example. It should be appreciated that other means such as, voice recognition software could be used to populate patient ID field 114 and patient name field 115. To start the test, a patient or an administrator presses the "Enter" button on a keyboard. The test can be started without inputting data into patient ID field 114 and patient name field 115. A user can exit testing software 100 by selecting exit button 105 located at the top right of subject data screen 116. FIGS. 3a and 3b represent enlarged enclosed areas 3a and 3b, respectively, shown in FIG. 3.

The CCT test can be implemented using any characters preferably, letters or numbers. For Dyslexic patients, conducting the test using numbers may yield more favorable results. To present the test with letters, press the R-CCT button on the remote control or the STAIR button on the screen. Using the keyboard, press Shift F1. To present the test with numbers, first select the NUM button on the remote control. Then press R-CCT on the remote control or the STAIR button on the screen.

Figure 4:
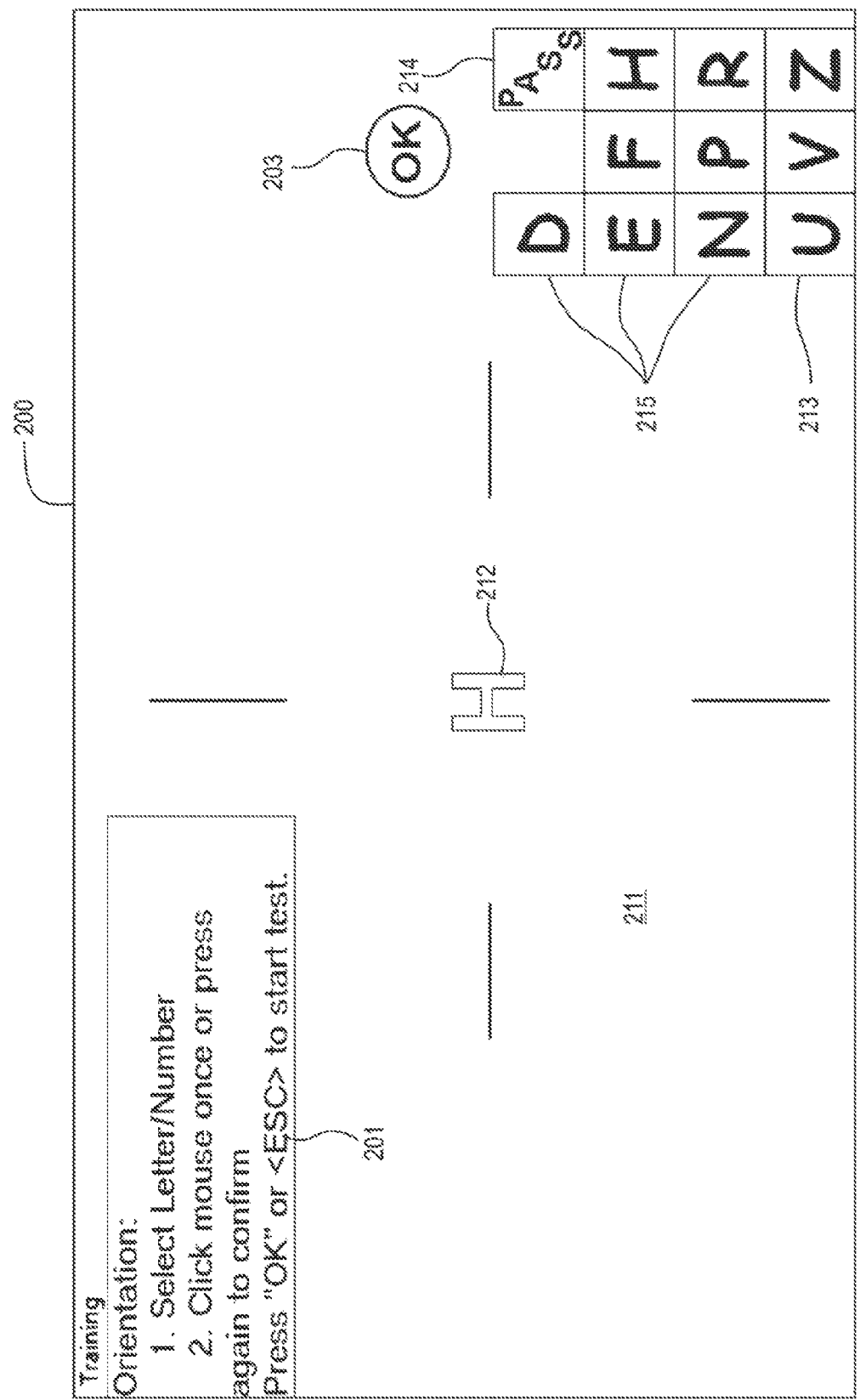
FIG. 4 is a screen shot of the invention.

FIG. 4 shows orientation testing screen 200. Orientation testing screen 200 comprises orientation instruction pane 201, confirmation button 203, testing field 211, testing symbol 212, response table 213, and pass button 214. Response table 213 comprises plurality of response symbols 215. In some embodiments of the invention, orientation testing screen 200 is displayed immediately upon commencement of the visual acuity test process. By displaying orientation testing screen 200 prior to other portions of the visual acuity test, the method of taking the visual acuity test can be relayed and practiced by the patient taking the visual acuity test. Orientation instruction pane 201 contains written instructions on the specific steps the patient taking the visual acuity test should take during the testing process. Orientation instruction pane 201 also contains instructions for advancing to the other portions of the visual acuity test.

In the embodiment of the invention shown in FIG. 4, the written instructions in orientation instruction pane 201 instruct the patient taking the visual acuity test to identify testing symbol 212 in testing field 211 and select the equivalent symbol from the plurality of response symbols 215 in response table 213. In some embodiments of the invention, the specific symbols included in response table 213 will be selected randomly, but in all embodiments of the invention, a symbol equivalent to testing symbol 212 must be one of response symbols 215 in response table 213.

This initial selection of one of the symbols of the plurality of response symbols 215 in response table 213 highlights the selected symbol for review by the patient. In some embodiments of the invention, selecting one of the plurality of response symbols 215 will cause testing software 100 to produce a sound corresponding to the symbol selected, such as saying the name of the letter if the plurality of response symbols 215 are letters. Selecting the same symbol again will act as a confirmation and indicate to testing software 100 that the patient believes the symbol selected from the plurality of response symbols 215 in response table 213 to be the same as the testing symbol 212.

If the patient taking the visual acuity test cannot identify testing symbol 212, the patient may select pass button 214. This will indicate to testing software 100 that the patient is unable to identify testing symbol 212. In some embodiments of the invention, selecting the pass button will be recorded as an incorrect identification for patient visual acuity assessment purposes.

Upon confirmation of a symbol from the plurality of response symbols 215 in response table 213 or selection of pass button 214, testing software 100 will record the response and orientation testing screen 200 will refresh. Upon refreshing, orientation testing screen will display a new testing symbol 212 and response table 213 will comprise a different plurality of response symbols 215. The patient taking the visual acuity test will then select one of the plurality of response symbols 215 in response table 213 or pass button 214, continuing the orientation process. When the patient is confident that he or she understands the method of taking the visual acuity test, the orientation process can be ended by selecting the confirmation button 203.

Figure 5:
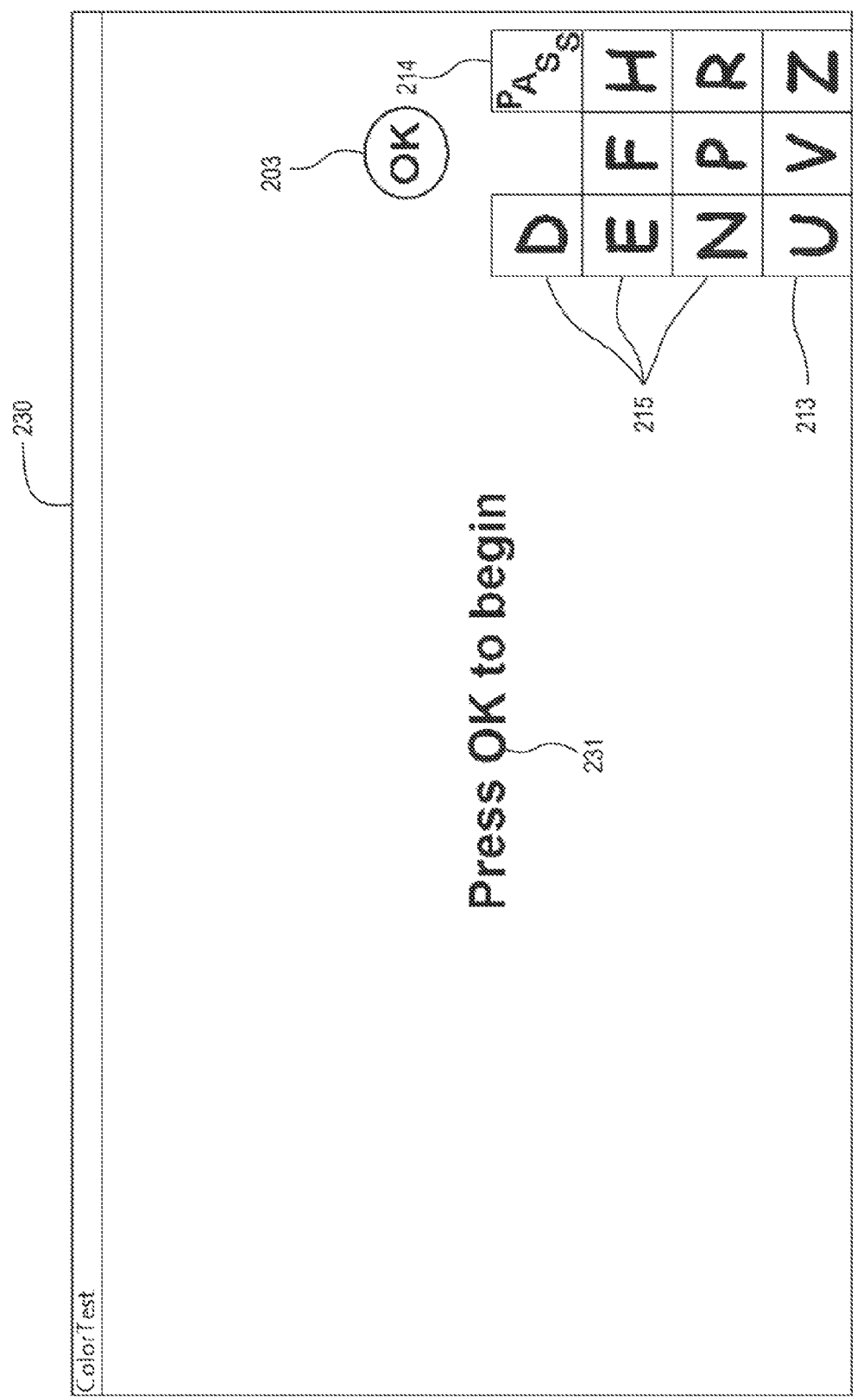
FIG. 5 is a screen shot of the invention.

FIG. 5 shows test commencement screen 230. Test commencement screen 230 comprises commencement message 231, confirmation button 203, response table 213, and pass button 214. Response table 213 comprises plurality of response symbols 215. Test commencement screen 230 is displayed immediately prior to the commencement of the testing portions of the visual acuity test to announce that the test process is ready to begin. The patient taking the visual acuity test will select confirmation button 203 when they are ready to begin the testing process. Although response table 213 and pass button 214 are components of test commencement screen 230, they are not active, i.e., they cannot be selected.

Figure 6:
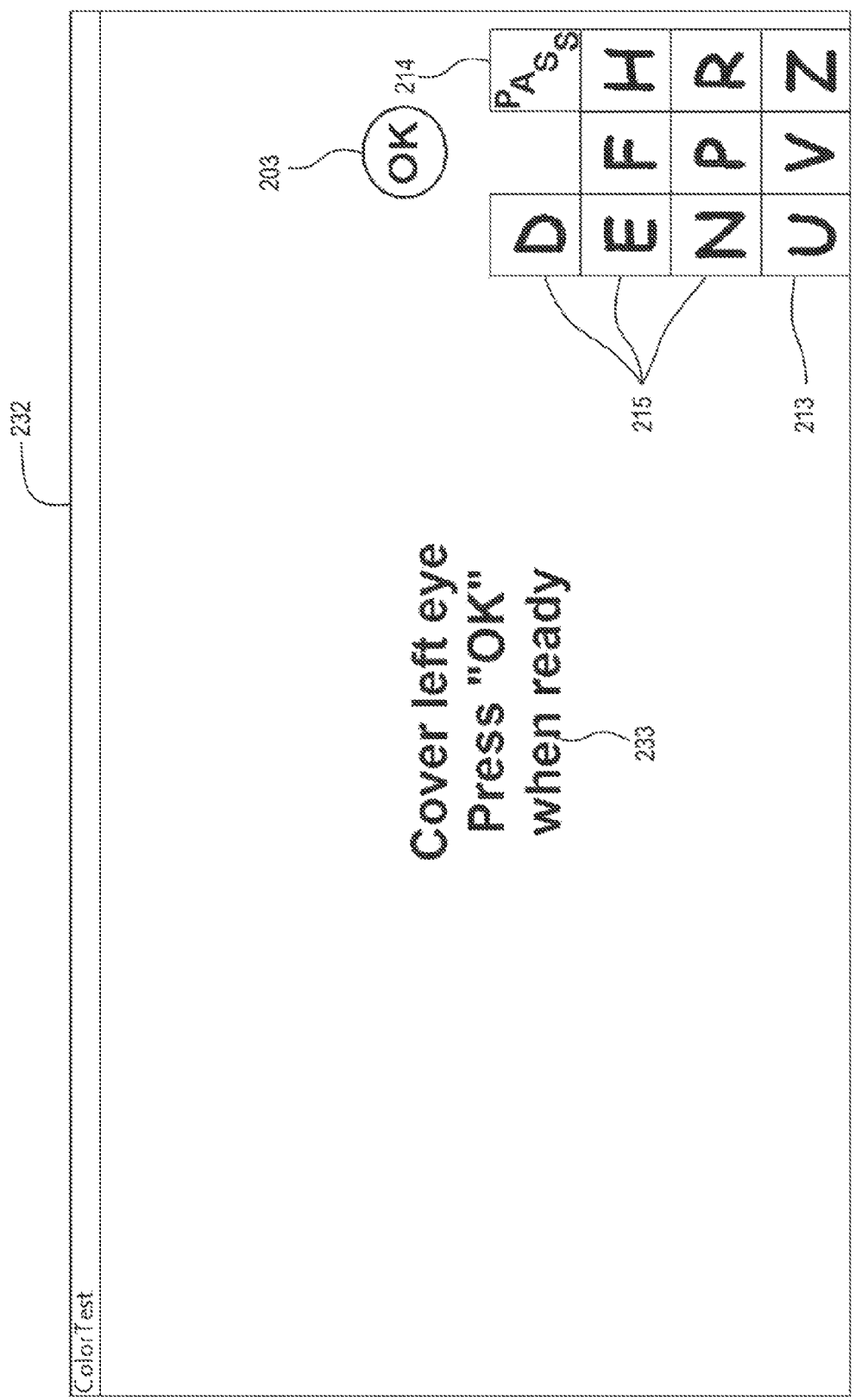
FIG. 6 is a screen shot of the invention.

FIG. 6 shows eye selection screen 232. Eye selection screen 232 comprises eye selection message 233, confirmation button 203, response table 213, and pass button 214. Response table 213 comprises plurality of response symbols 215. Eye selection screen 232 is displayed immediately prior to each of the two eye-specific portions of the visual acuity test. As visual acuity can be different in the left and right eyes of the patient taking the visual acuity test, it is beneficial to test the left and right eyes individually. By testing the left and right eyes individually, a more thorough understanding of the patient's visual acuity can be obtained.

Eye selection message 233 indicates which eye will be tested in the following test portion. For example, if the right eye is to be tested in the following test portion, eye selection message 233 would instruct the patient to cover their left eye and perform the test with their right eye only. The patient taking the visual acuity test will select confirmation button 203 when they are ready to begin the testing process for the eye indicated in eye selection message 233. Although response table 213 and pass button 214 are components of eye selection screen 232, they are not active, i.e., they cannot be selected.

Figure 7:
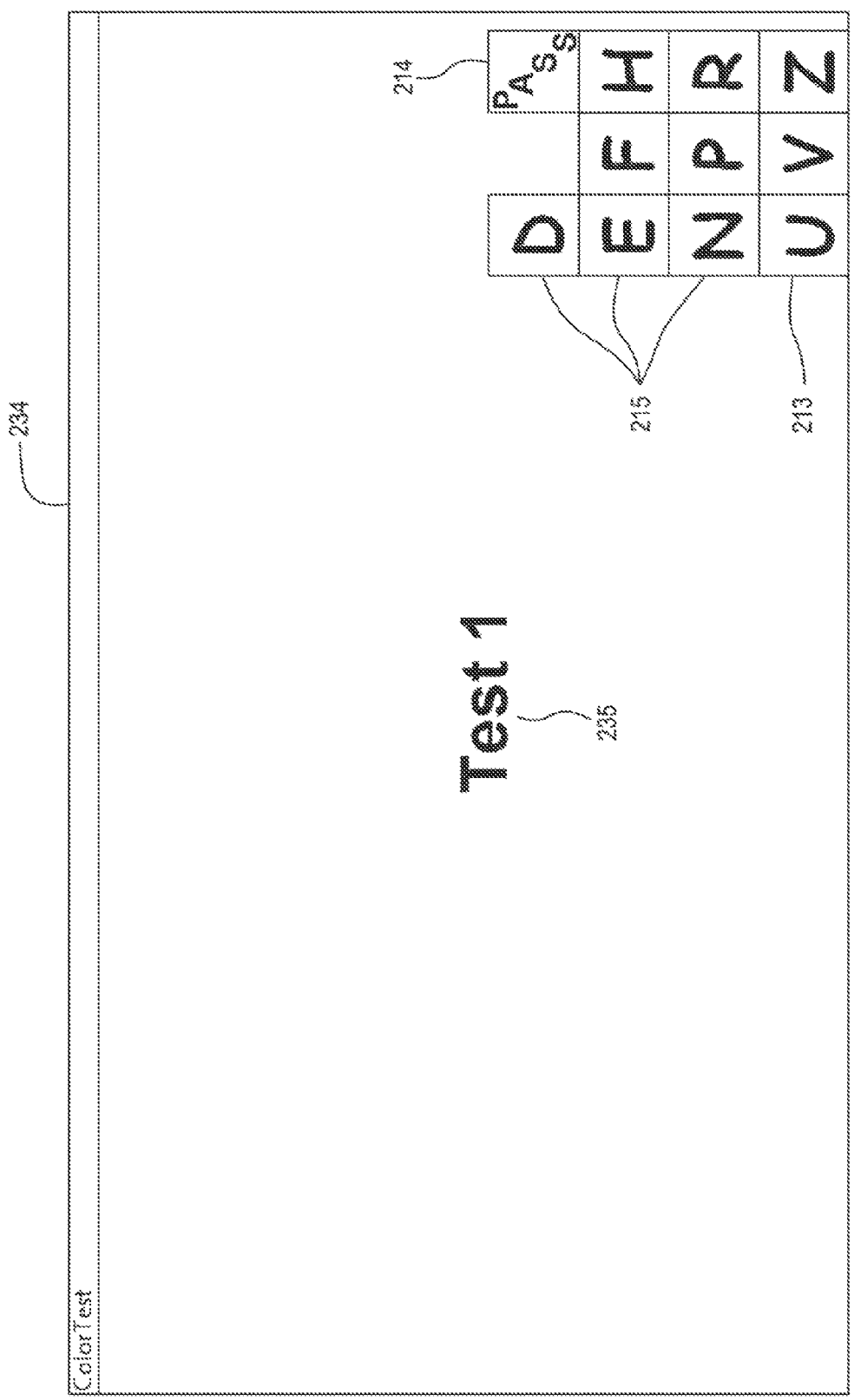
FIG. 7 is a screen shot of the invention.

FIG. 7 shows color phase screen 234. Color phase screen 234 comprises color phase message 235, response table 213, and pass button 214. Response table 213 comprises plurality of response symbols 215. Color phase screen 234 is displayed immediately prior to each of the three color-specific phases of the visual acuity test.

The ability of humans to perceive different colors of light is made possible by specialized cells in the retina called cone cells. Each of the three different types of cone cells detects a different portion of the visual spectrum, and each type is most sensitive to a certain color of light. The three different types of cone cells are most sensitive to colors that correspond approximately to the colors of red, green, and blue. Colors other than red, green, and blue are perceived via the combination in the human brain of signals from multiple types of cone cells and their relative intensities. For example, the color yellow is perceived when the red and green cone cells are stimulated approximately equally. The phenomenon of perceiving the full spectrum of visible light based on the combination of signals from three types of cells, each of which detects a different color, is called trichromasy.

As human vision is trichromatic, deficiencies in one or more of the types of cone cells can impair the ability of an individual to perceive certain colors. However, because each type of cone cell is most sensitive to a certain color of light, it is possible to individually assess the sensitivity of cone cells of a certain type by testing the ability to distinguish image components made of the color that the corresponding type of cone cell is most sensitive to. For this reason, the visual acuity test has three phases for each eye, a red phase, a green phase, and a blue phase. For example, in the red phase, the sensitivity of the red-type cone cells is assessed. In this way, the sensitivities of the red-type, green-type, and blue-type cone cells in each eye can be assessed.

Color phase message 235 announces to the patient taking the visual acuity test which color phase is about to begin. As the patient does not need to prepare for the specific color phases, the patient does not have to select any particular interface component to continue to the portion. The test process will continue automatically after a predetermined amount of time. Although response table 213 and pass button 214 are components of color phase screen 234, they are not active, i.e., they cannot be selected.

Figure 8:
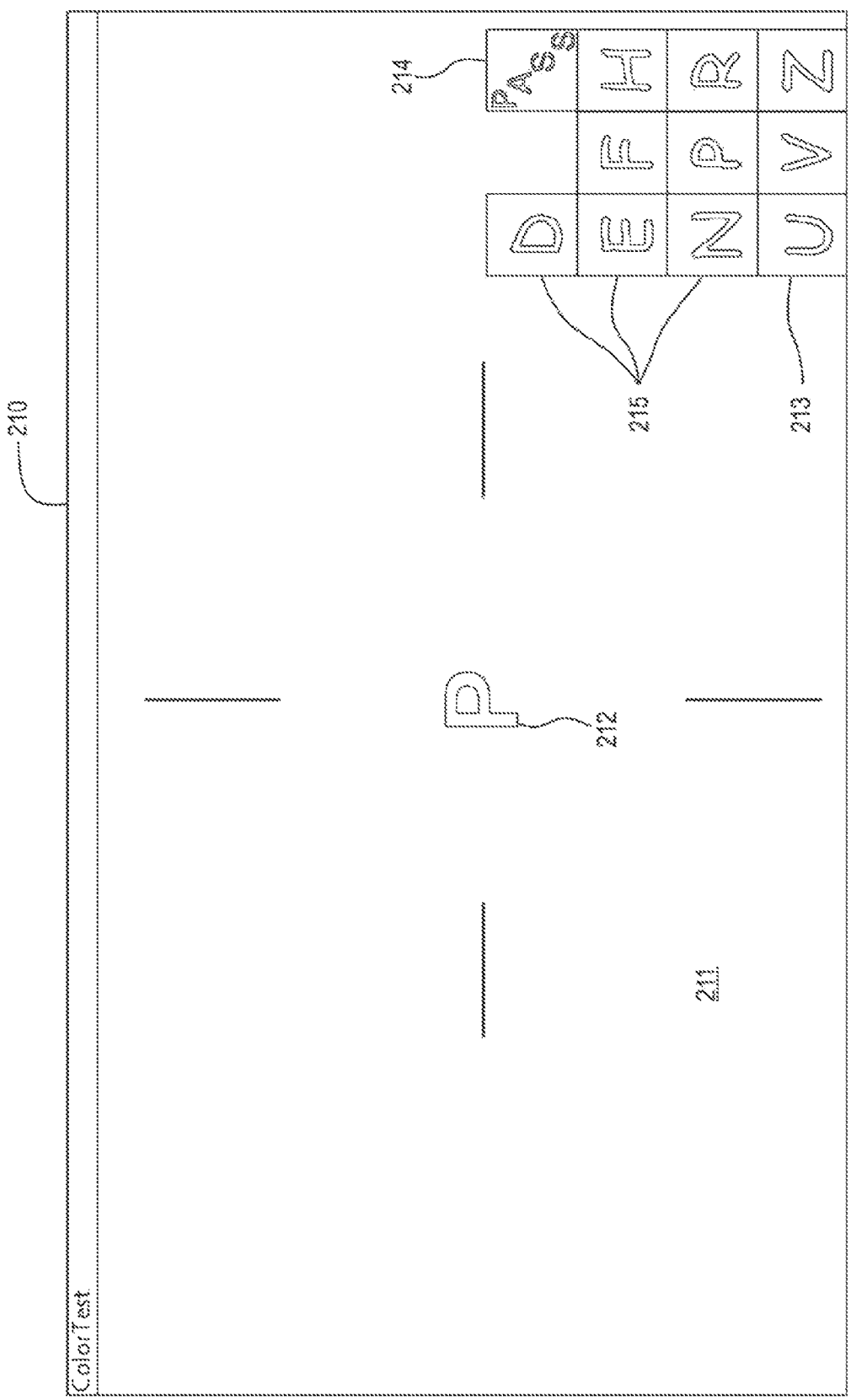
FIG. 8 is a screen shot of the invention.

FIG. 8 shows testing screen 210. Testing screen 210 comprises testing field 211, testing symbol 212, response table 213, and pass button 214. Response table 213 comprises plurality of response symbols 215. Having familiarized themselves with the testing method during the orientation portion of the visual acuity test, the patient taking the test will be able to perform the test without further instruction. Testing symbol 212, is either red, green, or blue, depending on which color phase the testing process is currently in. For example, in the red color phase of the testing process, testing symbol 212 will be red.

The sensitivities of the different types of cone cells is assessed by showing the patient taking the visual acuity test a testing symbol 212 of the color corresponding the present color phase on testing field 211. Initially, there is a large contrast differential between testing symbol 212 and testing field 211. Due to this high contrast differential, it is easier for the patient to distinguish the shape of testing symbol 212 and select the equivalent symbol from the plurality of response symbols 215 in response table 213. By iteratively reducing the contrast differential between testing symbol 212 and testing field 211 and asking the patient to select the equivalent symbol from the plurality of response symbols 215 in response table 213, until the patient is unable to correctly identify testing symbol 212, the ability of the specific cone cell types of the patient's specific eye can be assessed.

In some embodiments of the invention, the specific symbols included in response table 213 will be selected randomly, but in all embodiments of the invention, a symbol equivalent to testing symbol 212 must be one of response symbols 215 in response table 213.

This initial selection of one of the symbols of the plurality of response symbols 215 in response table 213 highlights the selected symbol for review by the patient. In some embodiments of the invention, selecting one of the plurality of response symbols 215 will cause testing software 100 to produce a sound corresponding to the symbol selected, such as saying the name of the letter if the plurality of response symbols 215 are letters. Selecting the same symbol again will act as a confirmation and indicate to testing software 100 that the patient believes the symbol selected from the plurality of response symbols 215 in response table 213 to be the same as the testing symbol 212.

If the patient taking the visual acuity test cannot identify testing symbol 212, the patient may select pass button 214. This will indicate to testing software 100 that the patient is unable to identify testing symbol 212. In some embodiments of the invention, selecting the pass button will be recorded as an incorrect identification for patient visual acuity assessment purposes. Additionally, in some embodiments of the invention, if the patient does not select any of the plurality of response symbols 215 in response table 213 in a predetermined amount of time, such inaction will be recorded as an incorrect identification for patient visual acuity assessment purposes. The predetermined amount of time before an incorrect identification is registered may be varied depending on the purpose of the visual acuity test. For example, if the purpose of the test is to measure the ability of piloting students to distinguish colors, the ability to make timely determinations may be more important than if the purpose of the test is to test generally for color-blindness. In such a case, the predetermined amount of time before an incorrect identification is registered may be reduced.

If the patient correctly identifies testing symbol 212 by selecting the equivalent symbol from the plurality of response symbols 215 in response table 213, testing software 100 will record a correct identification and continue the test process. In one embodiment of the invention, two correct identifications in succession by the patient at a specific contrast differential level will cause testing software 100 to display a testing screen 210 with a testing symbol 212 two contrast differential levels lower than the immediately preceding testing symbol 212.

If the patient selects an incorrect response symbol from the plurality of response symbols 215 in response table 213, then testing software 100 will record an incorrect identification. If the patient selects pass button 214, then testing software 100 will record that the patient chose to pass. In an embodiment of the invention, if the patient selects an incorrect response symbol from the plurality of response symbols 215 in response table 213, the testing software will display a testing screen 210 with a testing symbol 212 one contrast differential level higher than the immediately preceding testing symbol 212.

In yet another embodiment of the invention, if the patient correctly identifies two testing symbols 212 of a given contrast differential level, even if such correct identification is separated by an incorrect identification, or a selection of pass button 214, or the registering of an incorrect identification by the lapsing of the predetermined amount of time, then the testing software will display a testing screen 210 with a testing symbol 212 one contrast differential level lower than the immediately preceding testing symbol 212.

Generally, testing software 100 will start each phase of the test process by displaying a testing screen 210 with a testing symbol 212 of a maximum contrast differential with testing field 211. Upon registering a predetermined number of correct identifications of testing symbols 212, testing software 100 will begin displaying a series of testing screens 210 with testing symbols 212 of a lower contrast differential with testing field 211. Upon registering a predetermined number of incorrect identifications, or selections of pass button 214, or lapses of the predetermined amount of time, testing software 100 will begin displaying a series of testing screens 210 with testing symbols 212 of a higher contrast differential with testing field 211. The testing process in a specific color phase will end after a predetermined number of correct identifications are registered at a specific contrast differential level. Registering a large number of correct identifications at a specific contrast differential level indicates that the patient cannot reliably distinguish and identify a testing symbol 212 of lower contrast differential levels. The testing process in a specific color phase may also end after pass button 214 has been selected a predetermined number of times. Repeatedly selecting pass button 214 indicates that the patient can no longer reliably distinguish and identify the series of testing symbols 212 that are being displayed.

Figure 9:
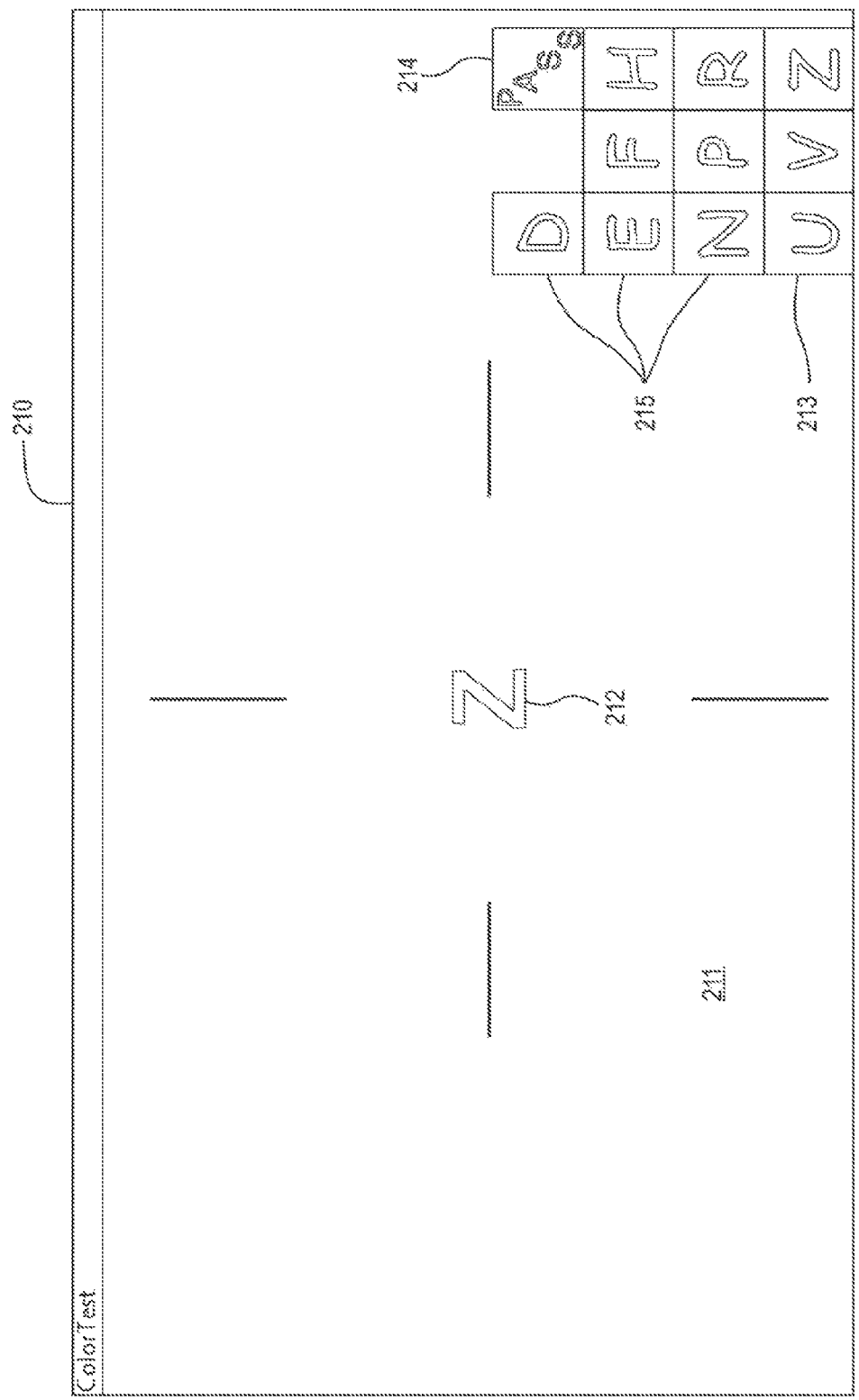
FIG. 9 is a screen shot of the invention.

FIG. 9 shows refreshed testing screen 210 comprising testing field 211, testing symbol 212 of reduced contrast differential with testing field 211, response table 213, and pass button 214. Response table 213 comprises plurality of response symbols 215. The patient taking the visual acuity test will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 10:
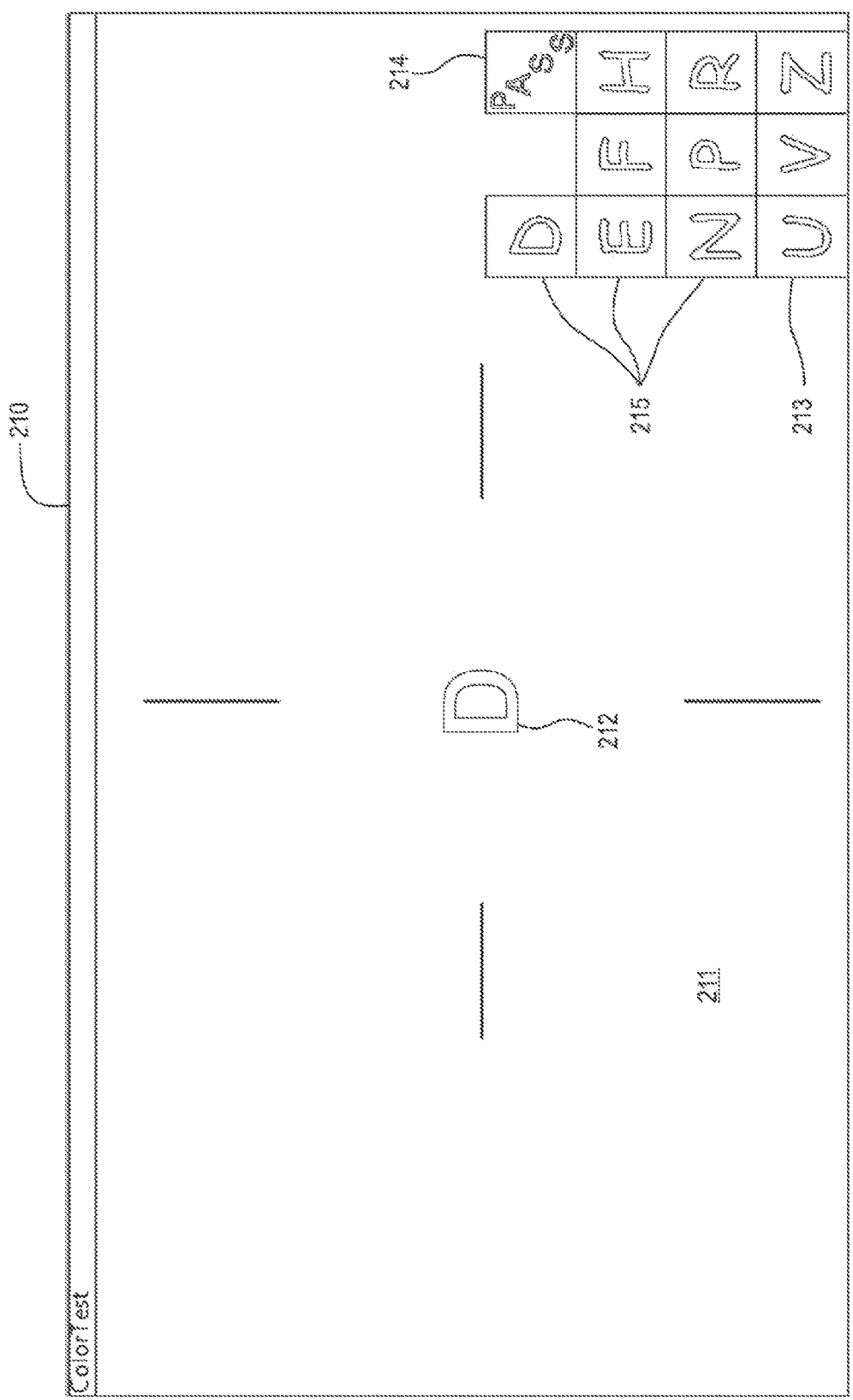
FIG. 10 is a screen shot of the invention.

FIG. 10 shows refreshed testing screen 210 comprising testing field 211, testing symbol 212 of further reduced contrast differential with testing field 211, response table 213, and pass button 214. Response table 213 comprises plurality of response symbols 215. The patient taking the visual acuity test will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 11:
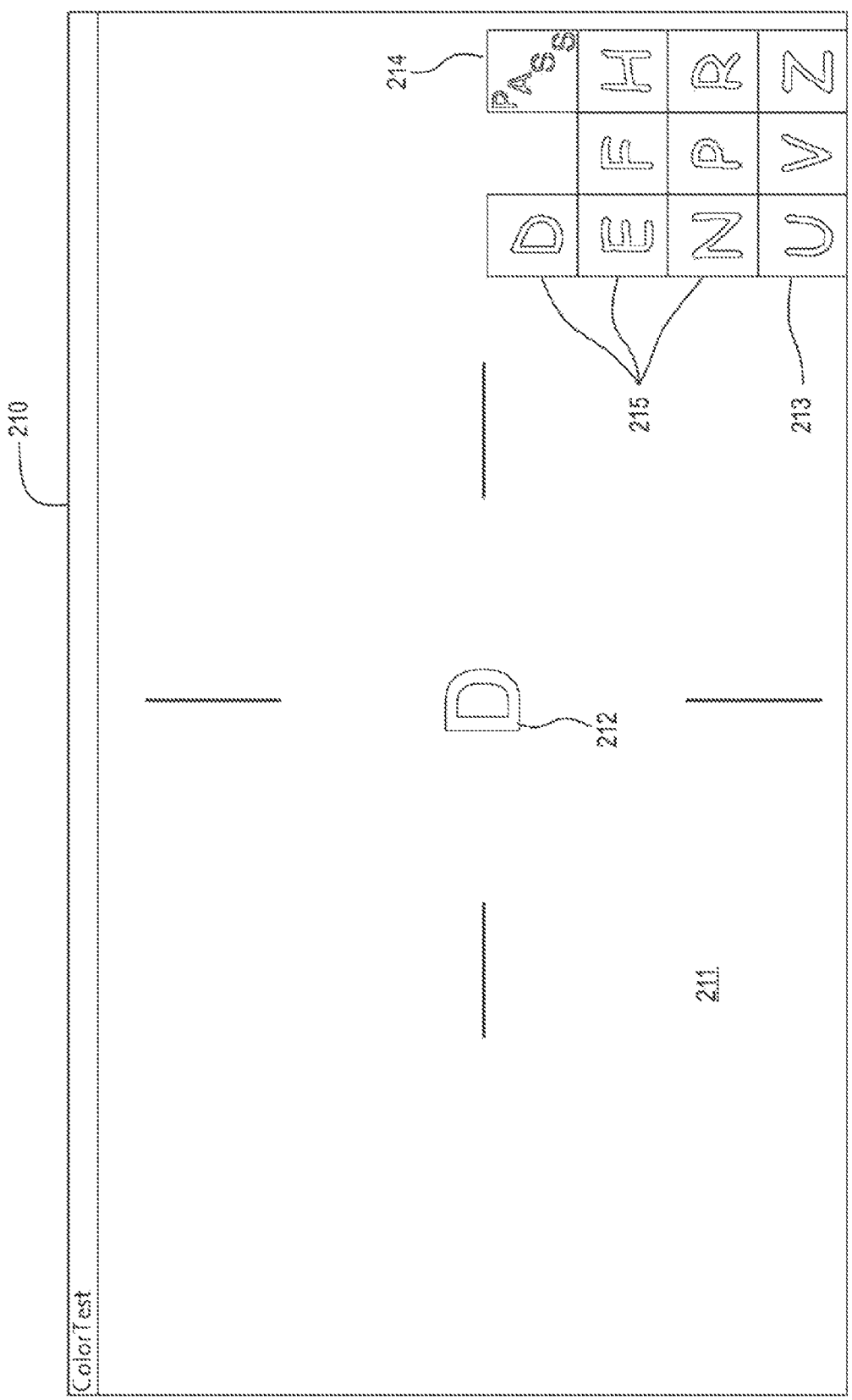
FIG. 11 is a screen shot of the invention.

FIG. 11 shows refreshed testing screen 210 comprising testing field 211, testing symbol 212 of even further reduced contrast differential with testing field 211, response table 213, and pass button 214. Response table 213 comprises plurality of response symbols 215. The patient taking the visual acuity test will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Figure 12:
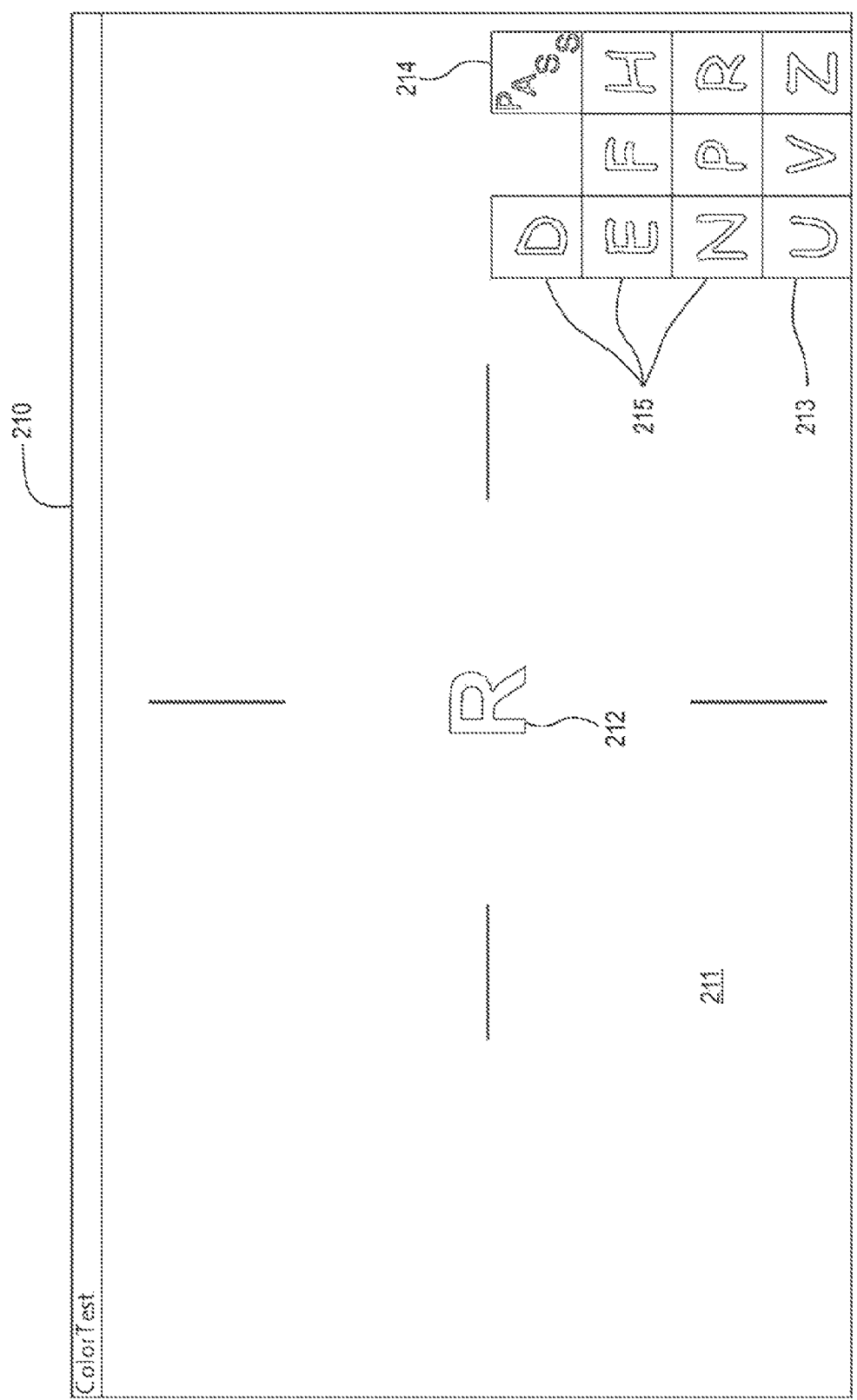
FIG. 12 is a screen shot of the invention.

FIG. 12 shows refreshed testing screen 210 comprising testing field 211, testing symbol 212 of minimal contrast differential with testing field 211, response table 213, and pass button 214. Response table 213 comprises plurality of response symbols 215. The patient taking the visual acuity test will attempt to correctly distinguish and identify testing symbol 212 and select the corresponding symbol from the plurality of response symbols 215. If the patient is unable to distinguish and identify testing symbol 212, they may select pass button 214 to cause testing software 100 to display new testing screen 210.

Upon completion of a specific color phase in the testing process, testing software 100 will continue to the next color phase for the currently tested eye. If all color phases have been completed for the currently tested eye, testing software 100 will display eye selection screen 232 and continue the testing process with the next eye to be tested. If all color phases for both eyes have been completed, the test process is complete.

Figure 13:
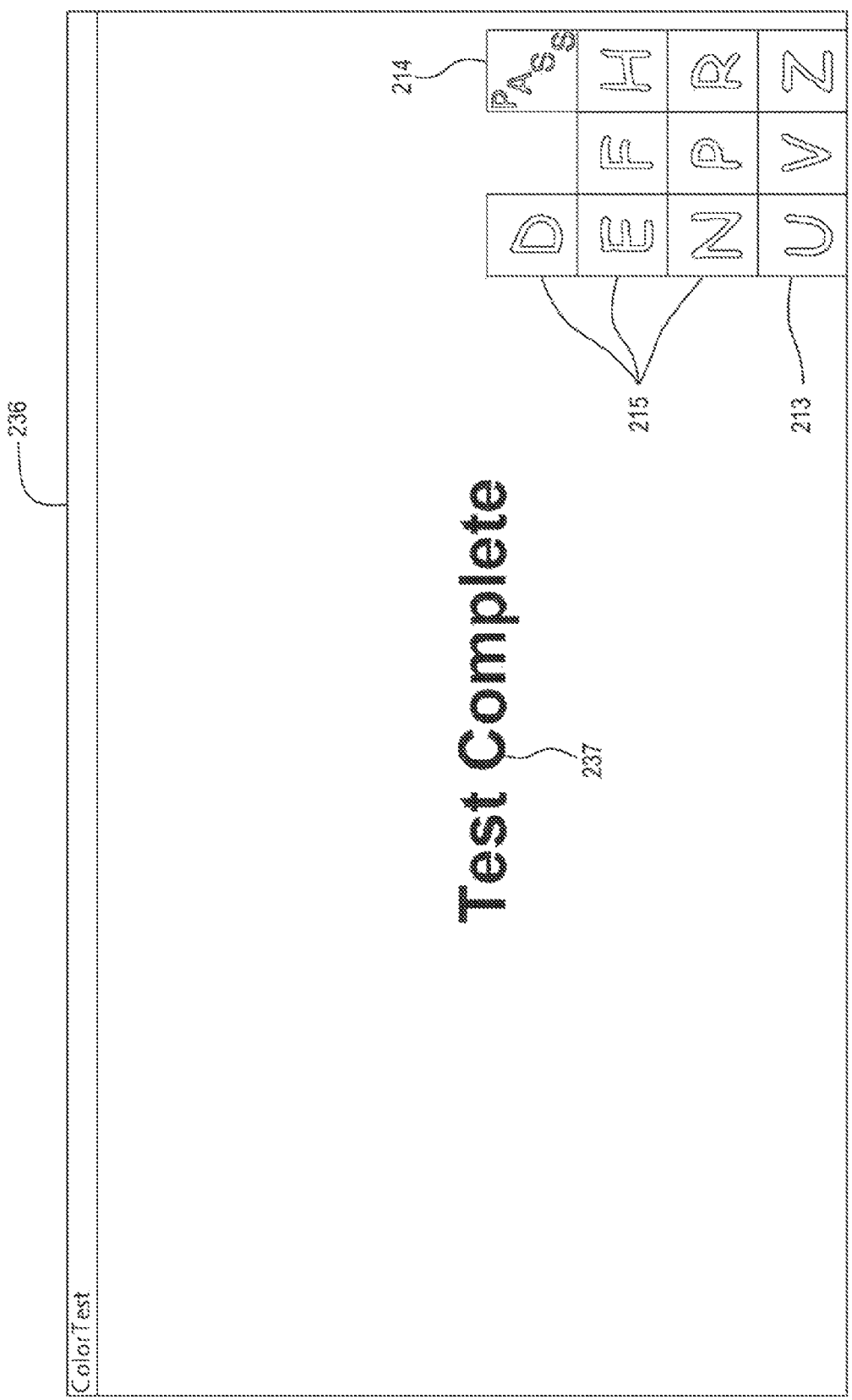
FIG. 13 is a screen shot of the invention.

FIG. 13 shows test conclusion screen 236. Test conclusion screen 236 comprises conclusion message 237, response table 213, and pass button 214. Conclusion message 237 informs the patient that the test process is complete. Although response table 213 and pass button 214 are components of test commencement screen 230, they are not active, i.e., they cannot be selected.

Viewing and Interpreting Results

Figure 19:
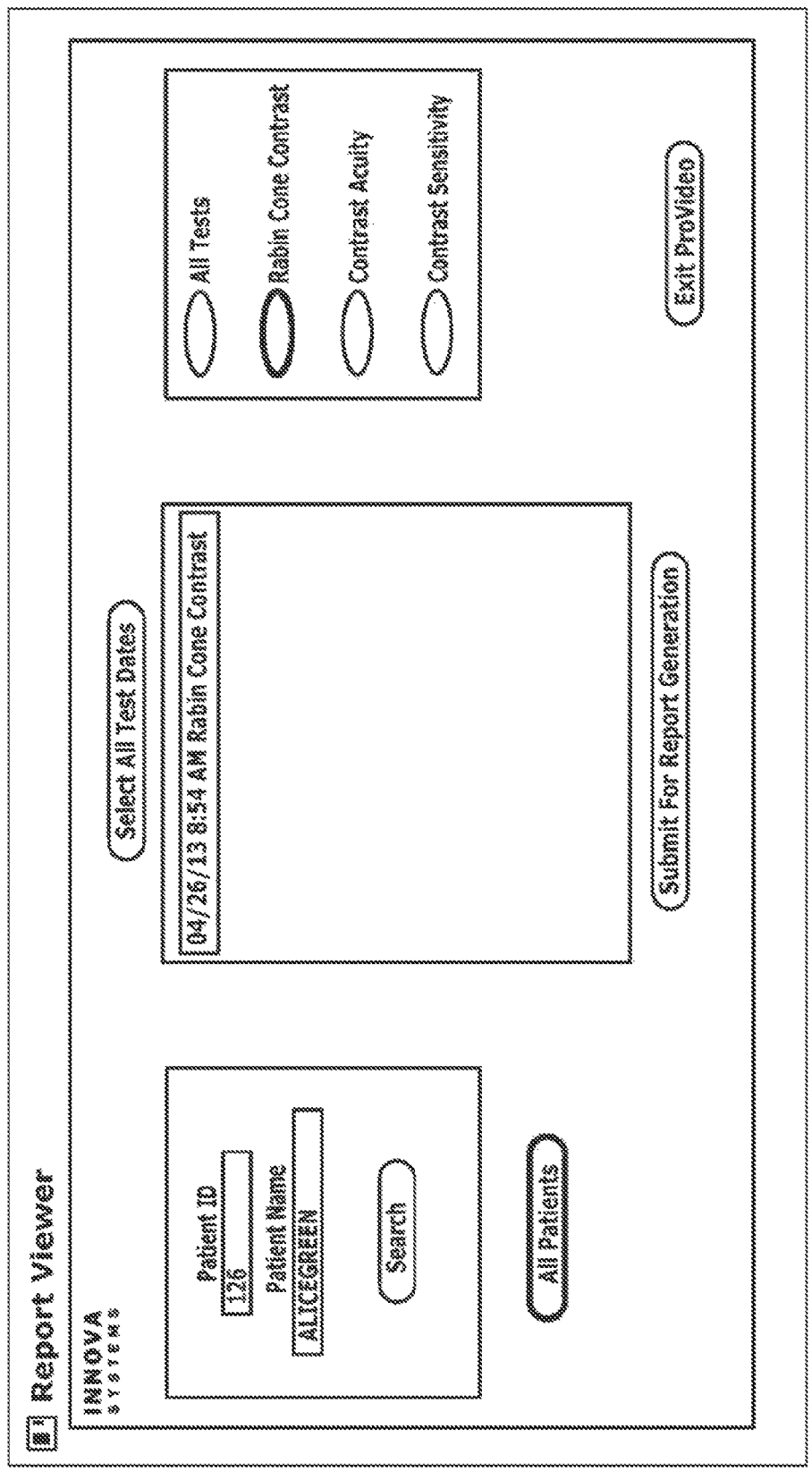
FIG. 19 is a screen shot of the invention.
Figure 20:
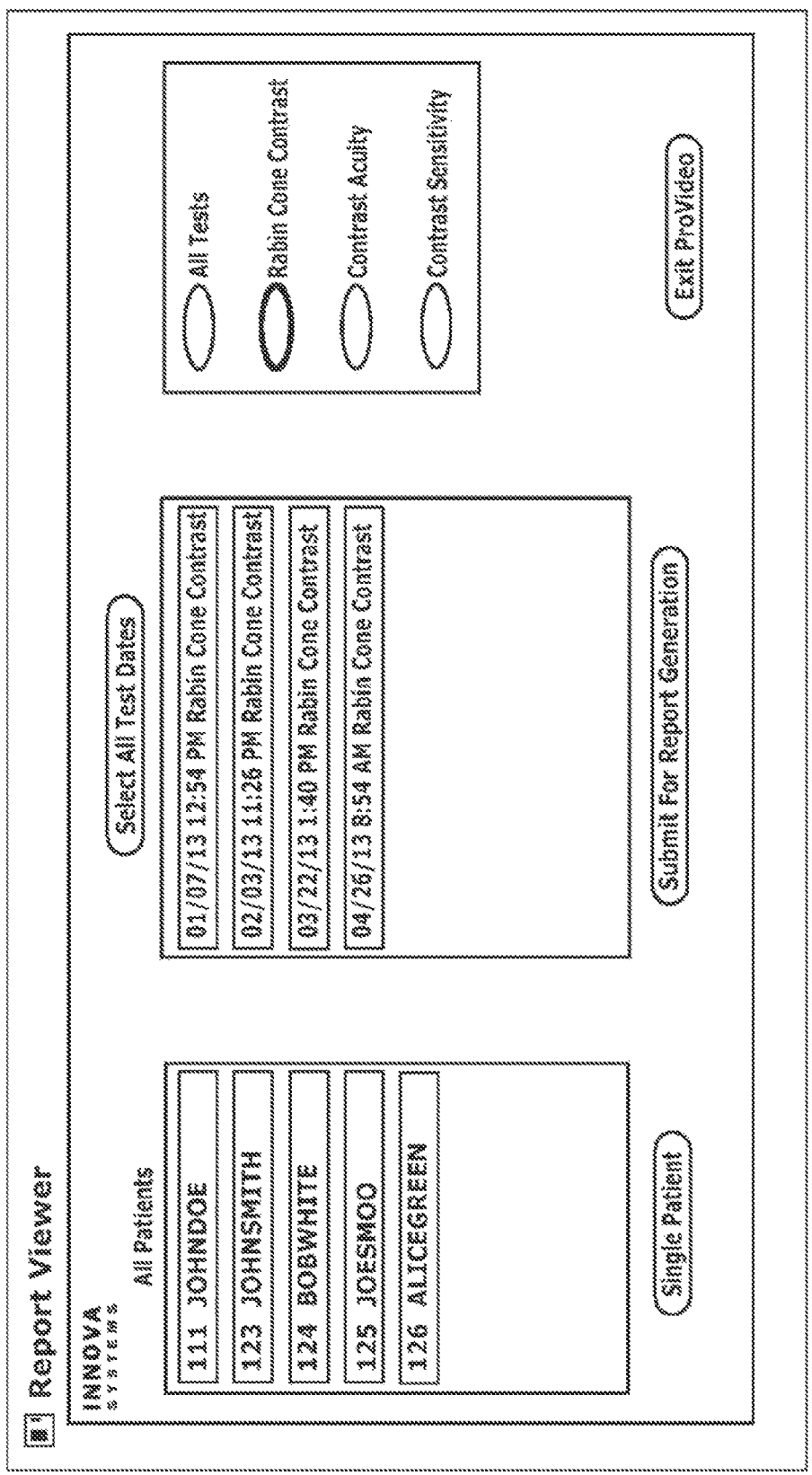
FIG. 20 is a screen shot of the invention.
Figure 21:
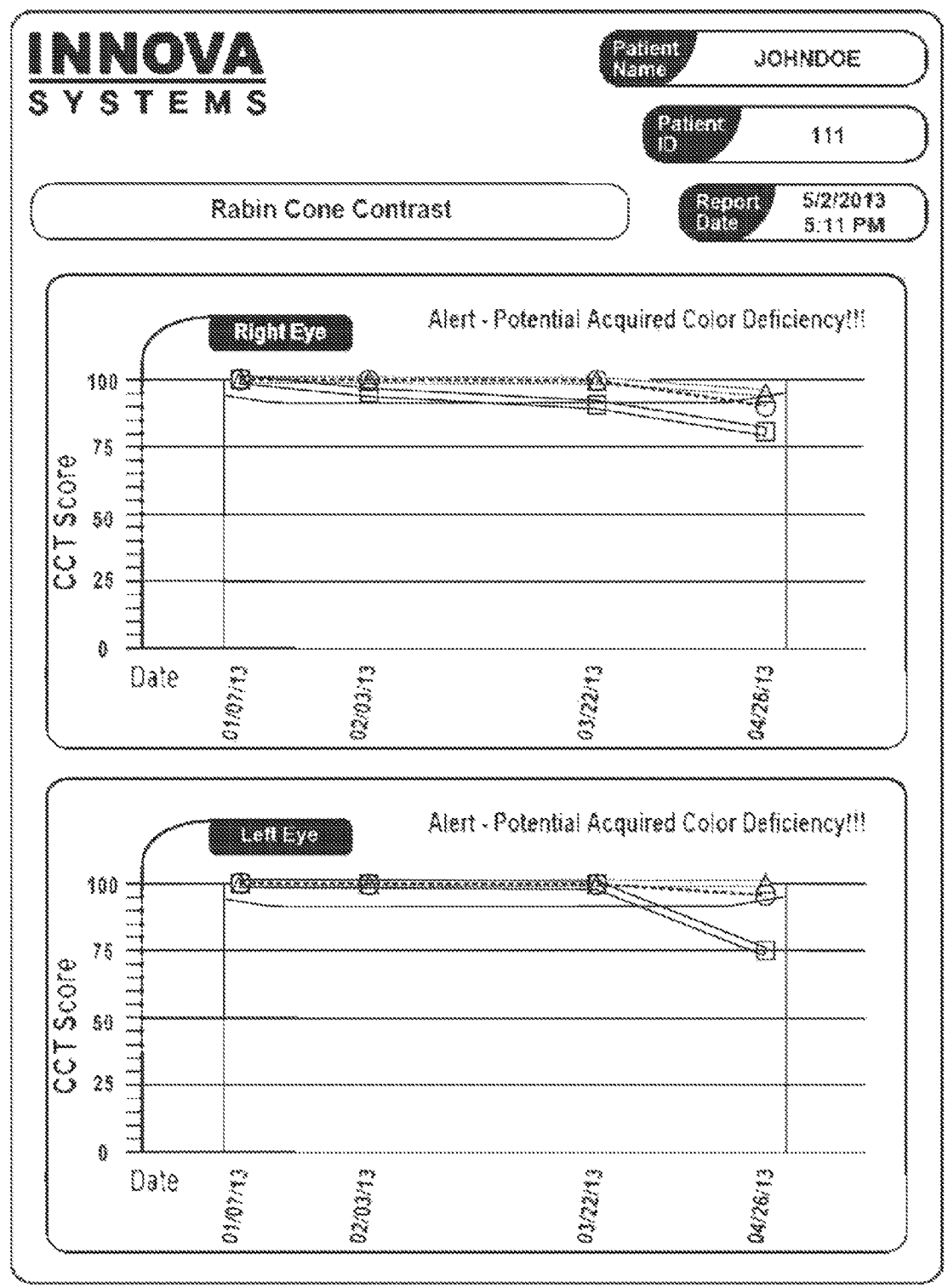
FIG. 21 is a report of the invention.
Figure 22:
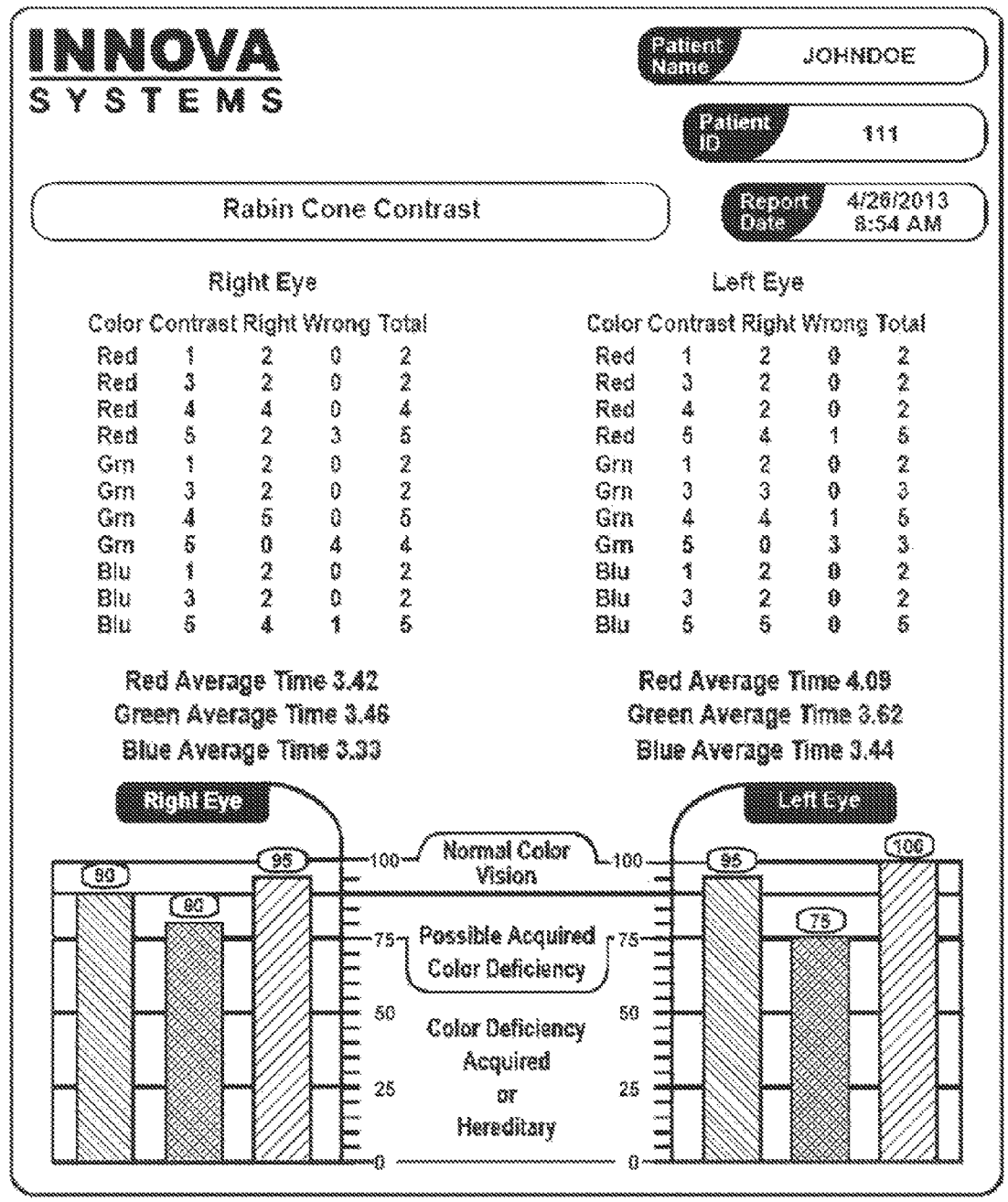
FIG. 22 is a report of the invention.

Reports may be generated by patient, type of report, and dates. To generate a report for a particular patient, testing software 100 is arranged to select data connected to a patient ID. You may display a list of all tests for a patient as shown in FIG. 19. Or, to print Comparison Reports, select the type of report to be displayed, and then select the date range for the report. Use the mouse or TAB key to move between the types of reports. Double click or hit ENTER on the specific report date to view specific exam results. Selecting Dates for Comparison Reports to view comparison results select the date range to be displayed. To display reports within a narrower time frame, for example, since the beginning of treatment, you may select a subset of the available tests. Hold down the SHIFT key to select a date range or hold down the CTRL key to select specific tests. Use the PgUp and PgDn buttons to select larger date ranges. When the desired test dates are selected, click or TAB to the Submit for Report Generation button to view the report.

Figure 14:
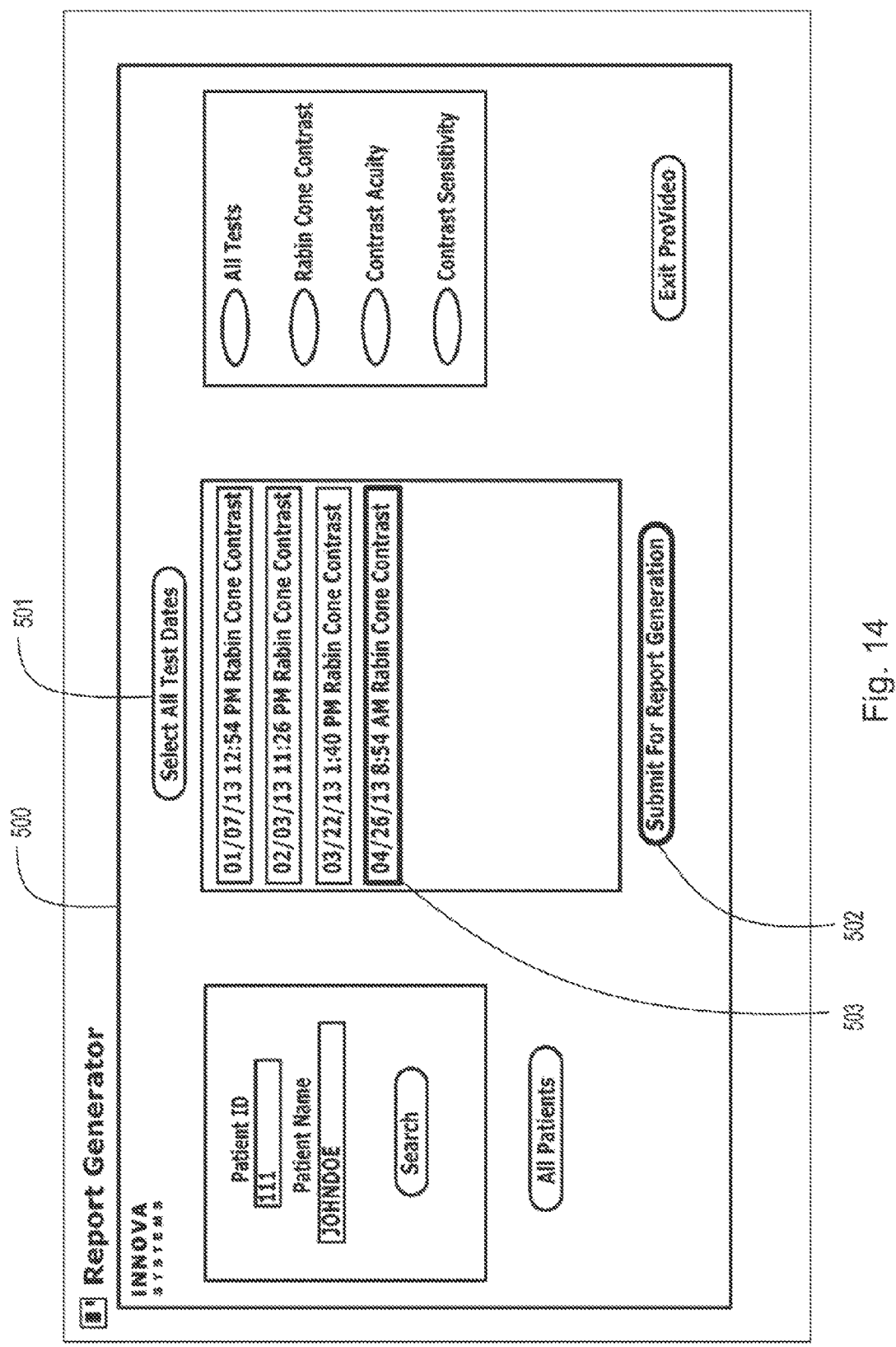
FIG. 14 is a screen shot of the invention.
Figure 15:
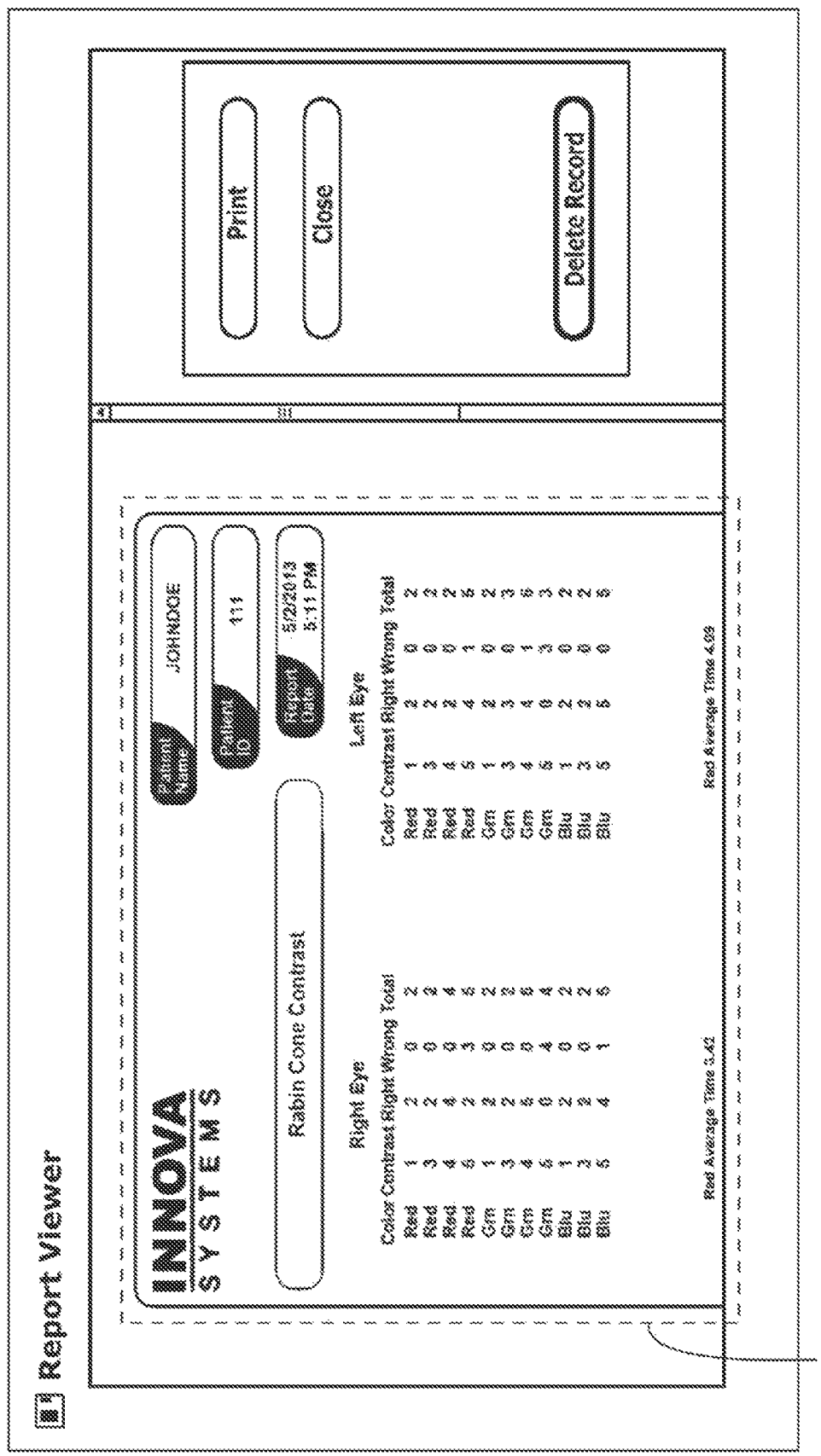
FIG. 15 is a report of the invention.
Figure 15A:
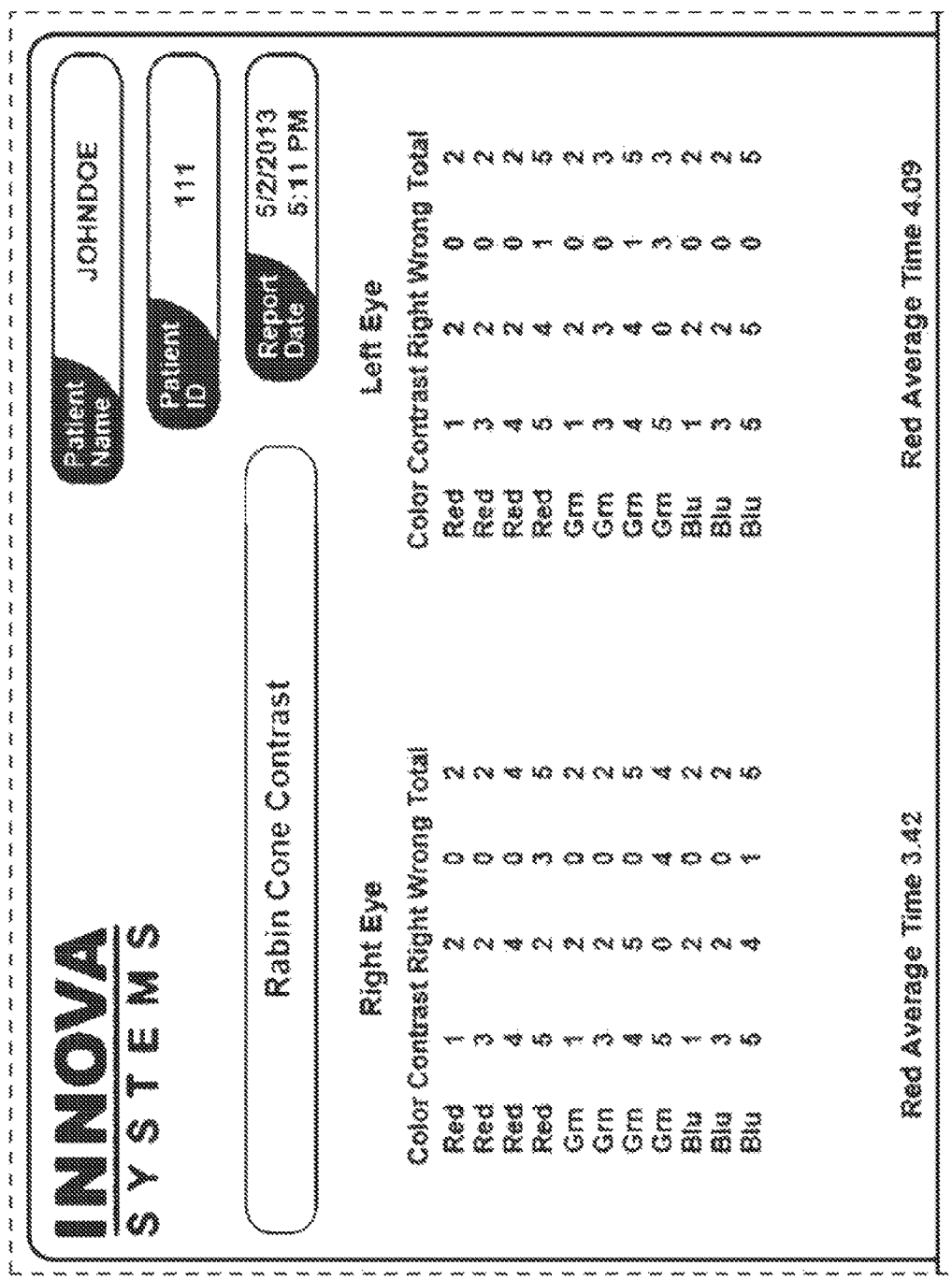
FIG. 15a is an enlarged view of the enclosed region 15a shown in FIG. 15.
Figure 16:
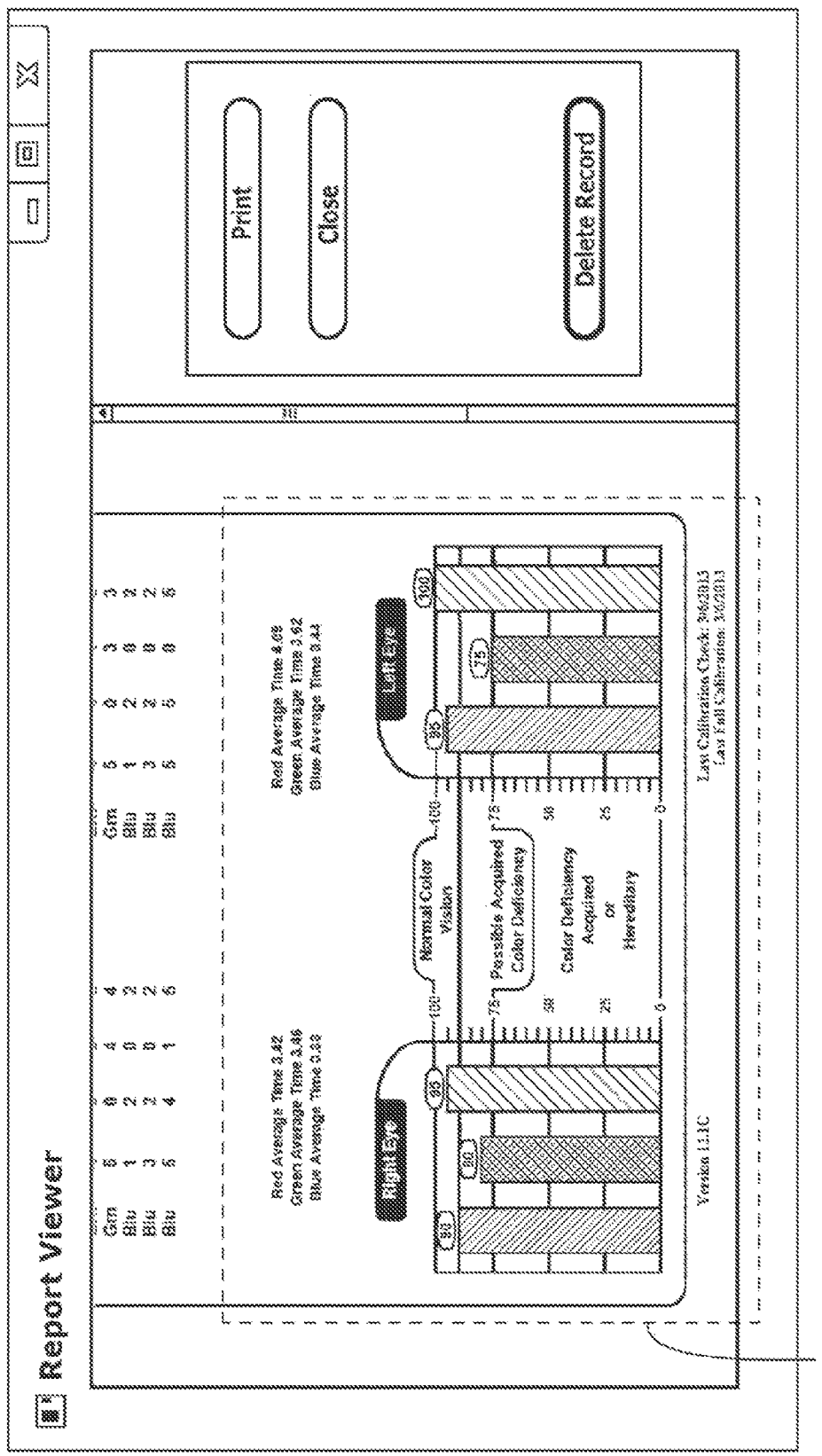
FIG. 16 is a report of the invention.
Figure 16A:
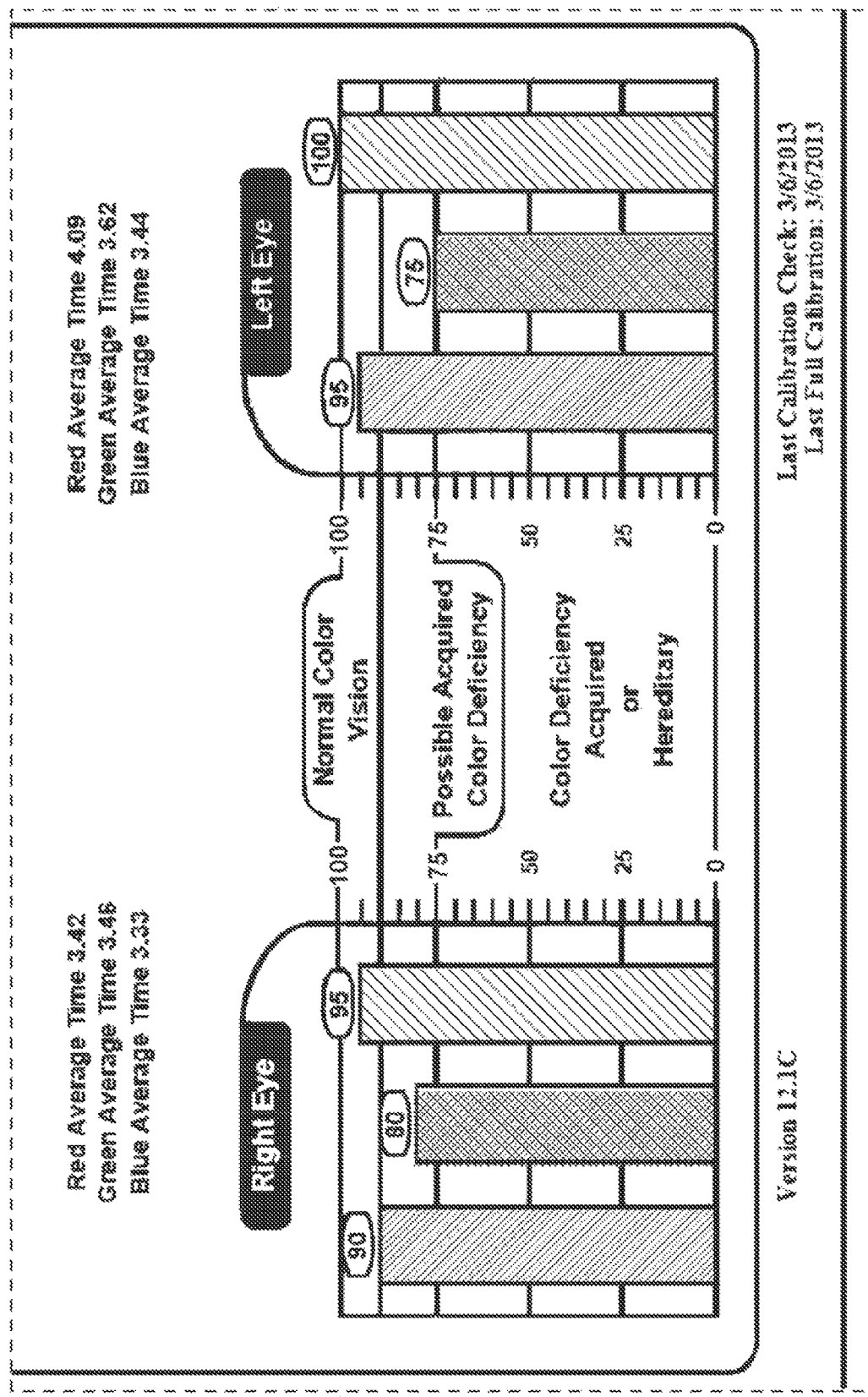
FIG. 16a is an enlarged view of the enclosed region 16a shown in FIG. 16.

Reports button 113 shown in FIG. 2 can be accessed to review and generate test results. Similarly, FIG. 14 shows report generator screen 500. Report generator screen 500 comprises select all test dates button 501 and submit for report generation button 502. If select all test dates button 501 is selected, testing software 100 is directed to include all test data in generating reports for interpretation. If select all test dates button 501 is not selected, particular test dates can be selected from report generator screen 500. Once particular test dates are selected from report generator screen 500, for example, selected test date 503, selection of submit for report generation button 502 directs testing software 100 to generate reports.

Figure 17:
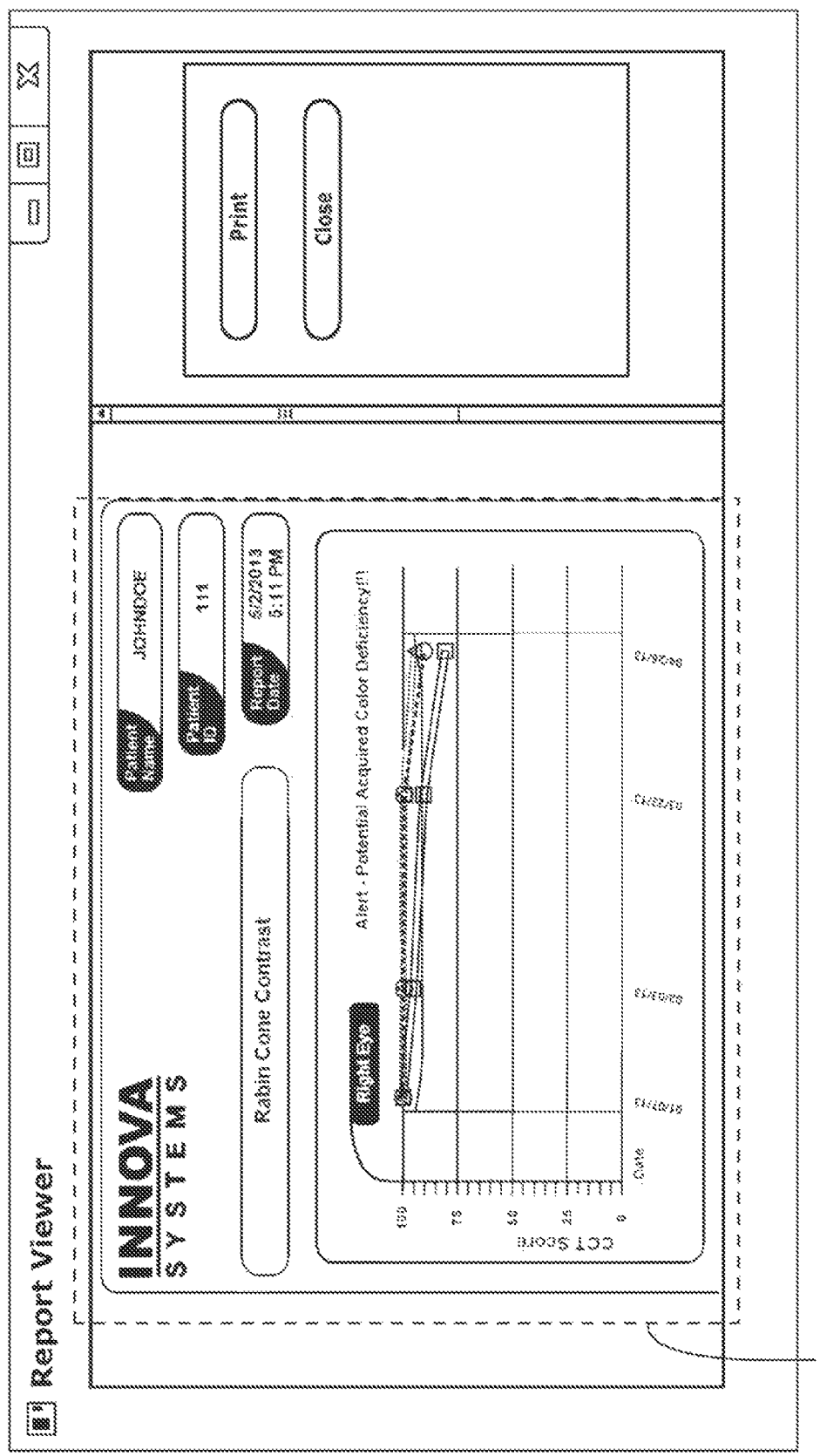
FIG. 17 is a report of the invention.
Figure 17A:
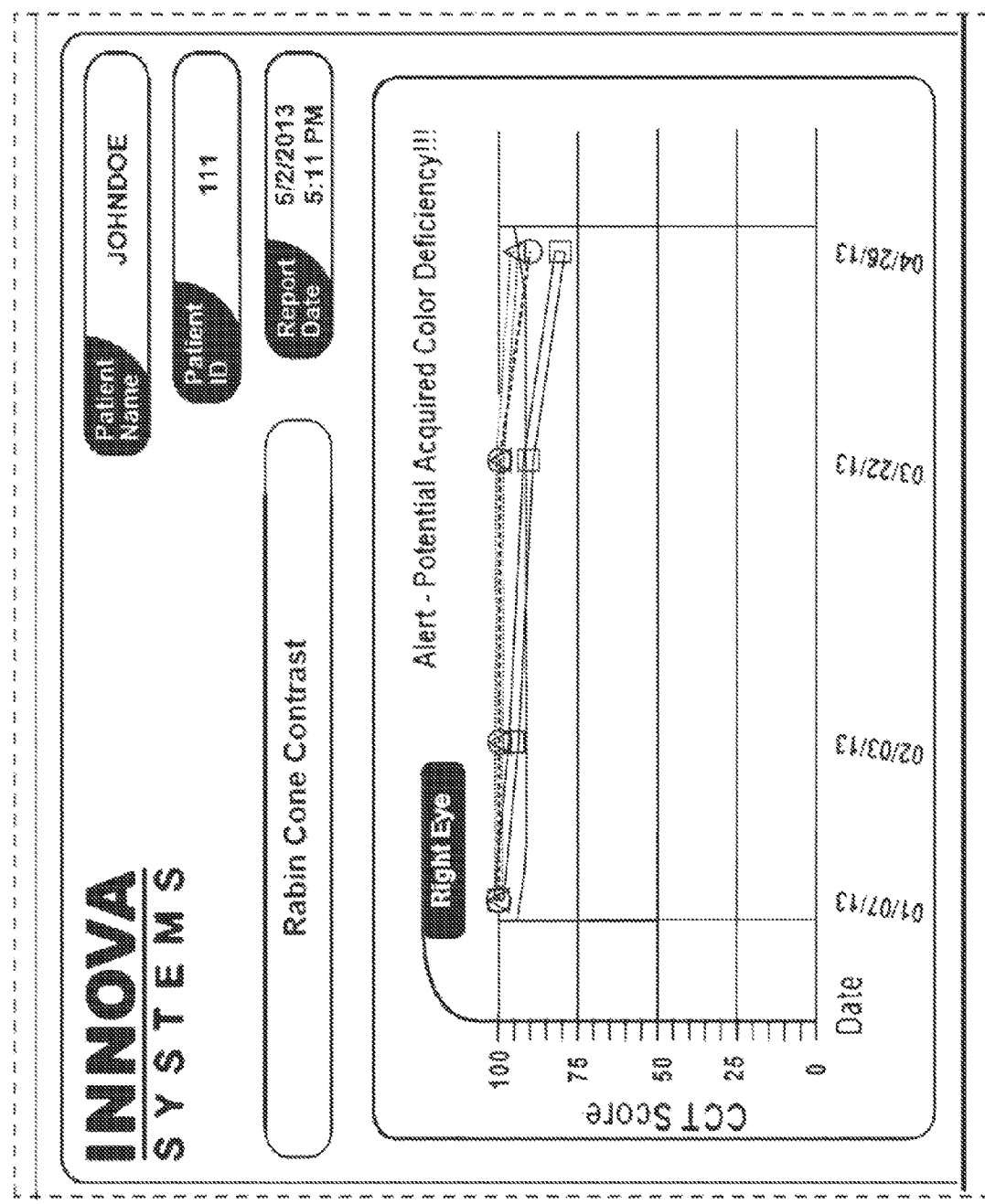
FIG. 17a is an enlarged view of the enclosed region 17a shown in FIG. 17.
Figure 18:
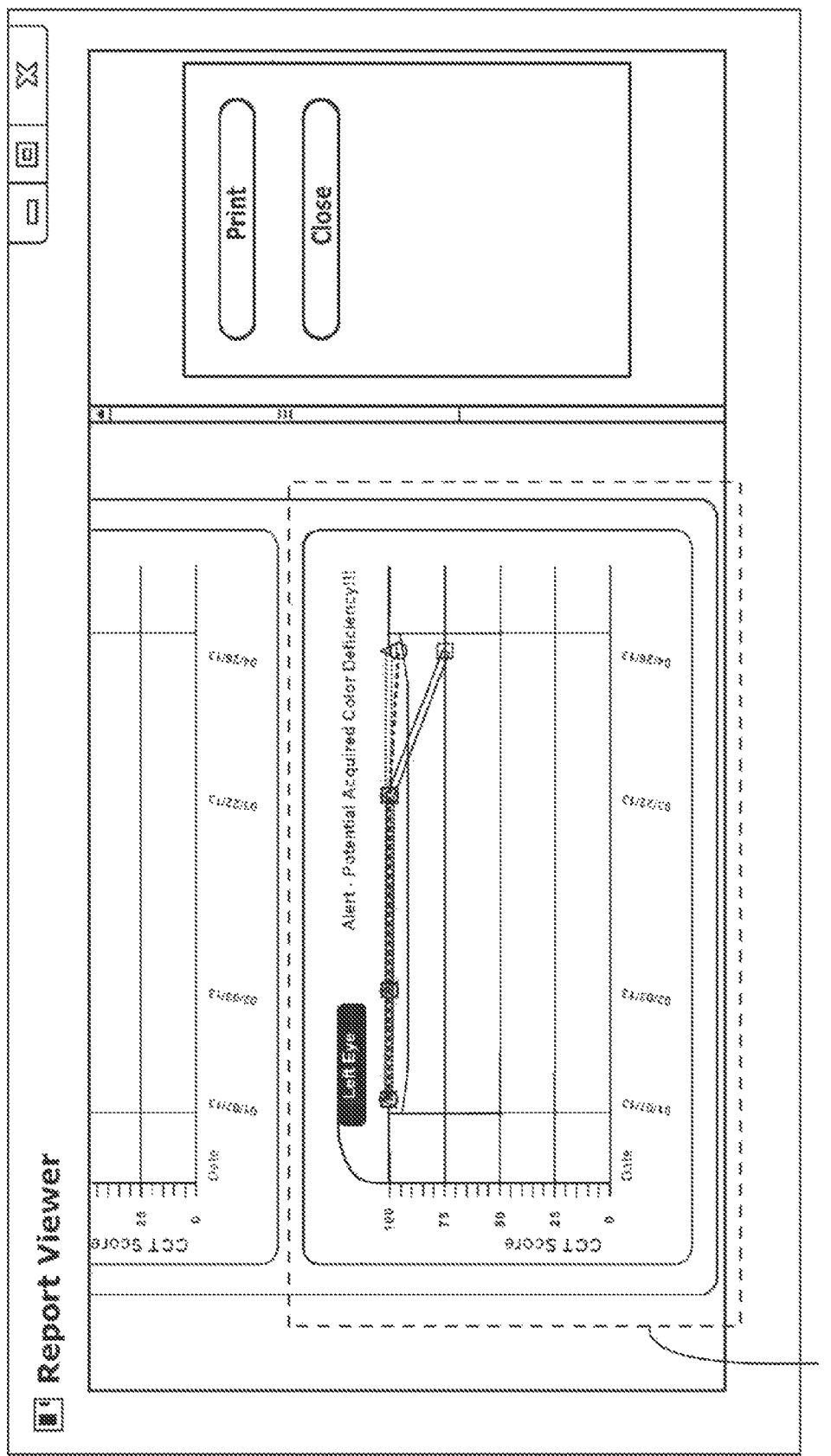
FIG. 18 is a report of the invention.
Figure 18A:
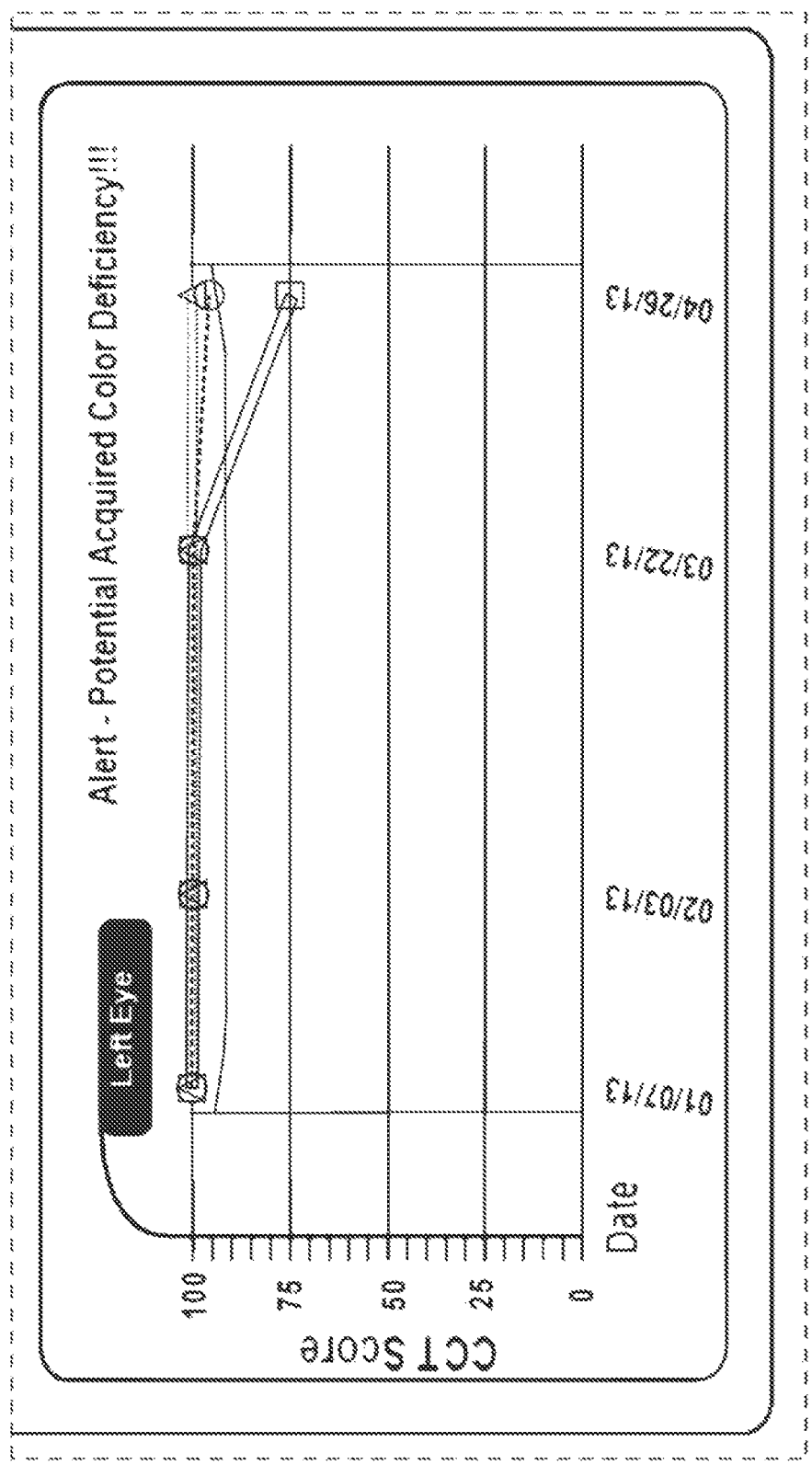
FIG. 18a is an enlarged view of the enclosed region 18a shown in FIG. 18.
Figure 23:
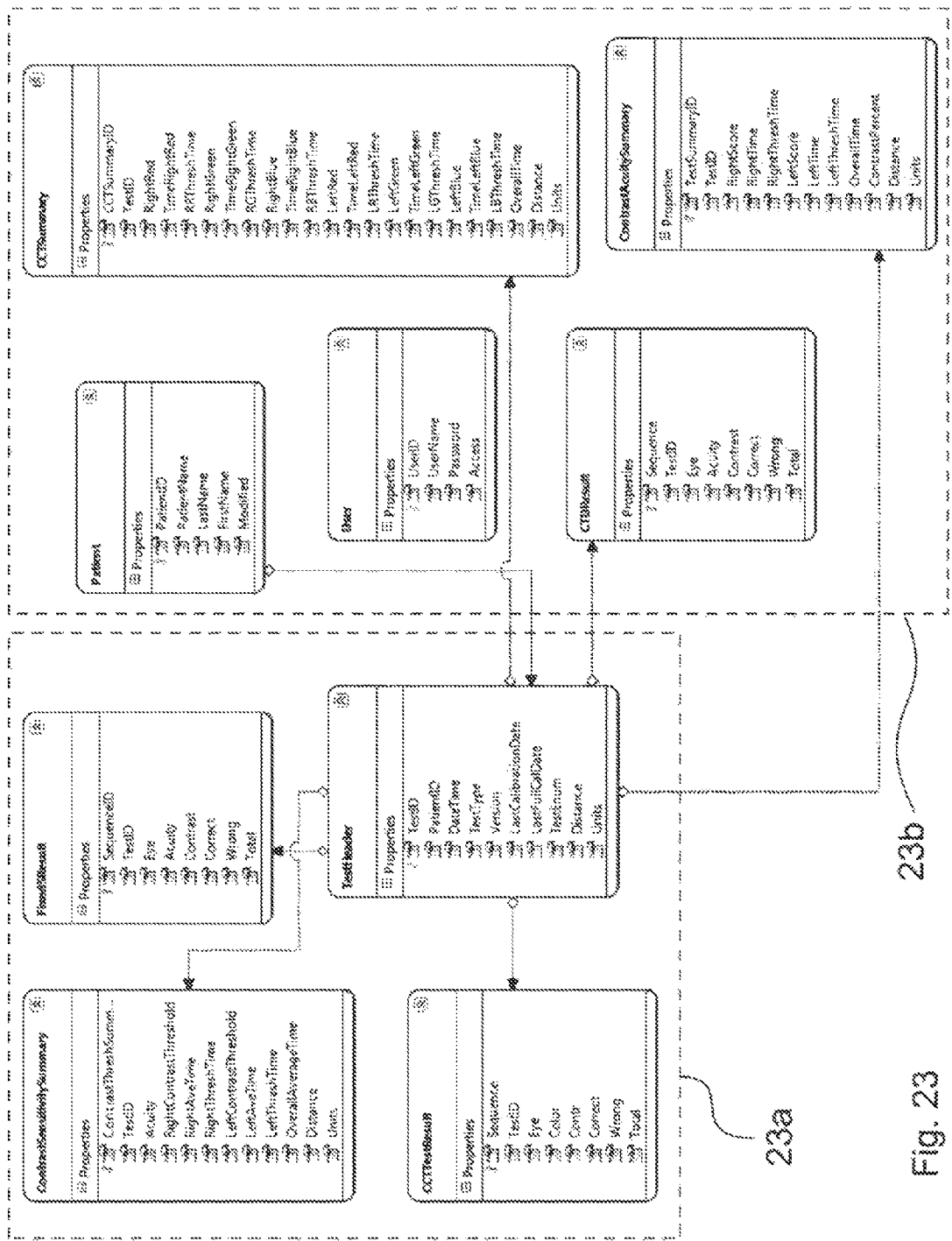
FIG. 23 is a diagram of the invention.
Figure 23A:
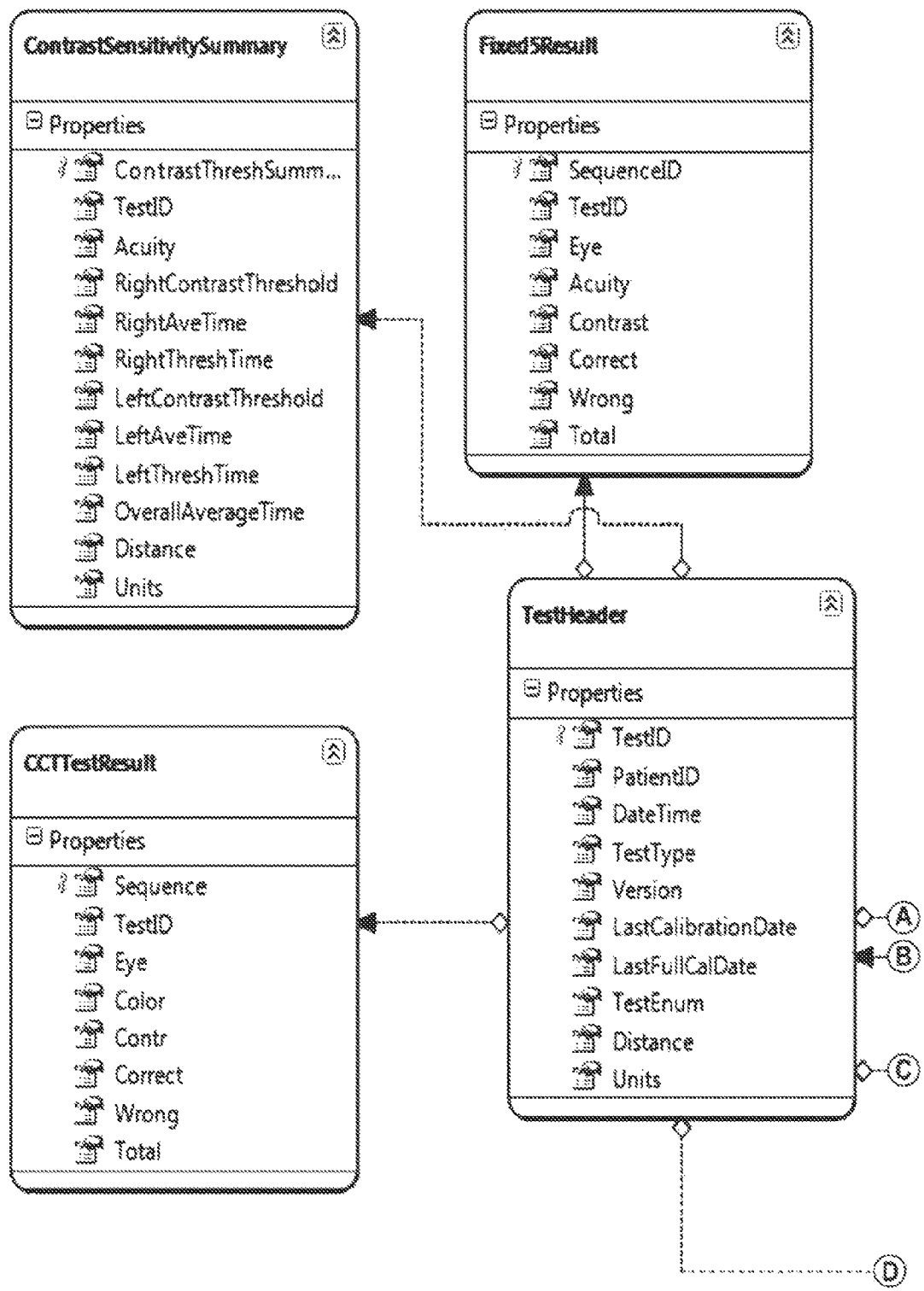
FIG. 23a is an enlarged view of the enclosed region 23a shown in FIG. 23.
Figure 23B:
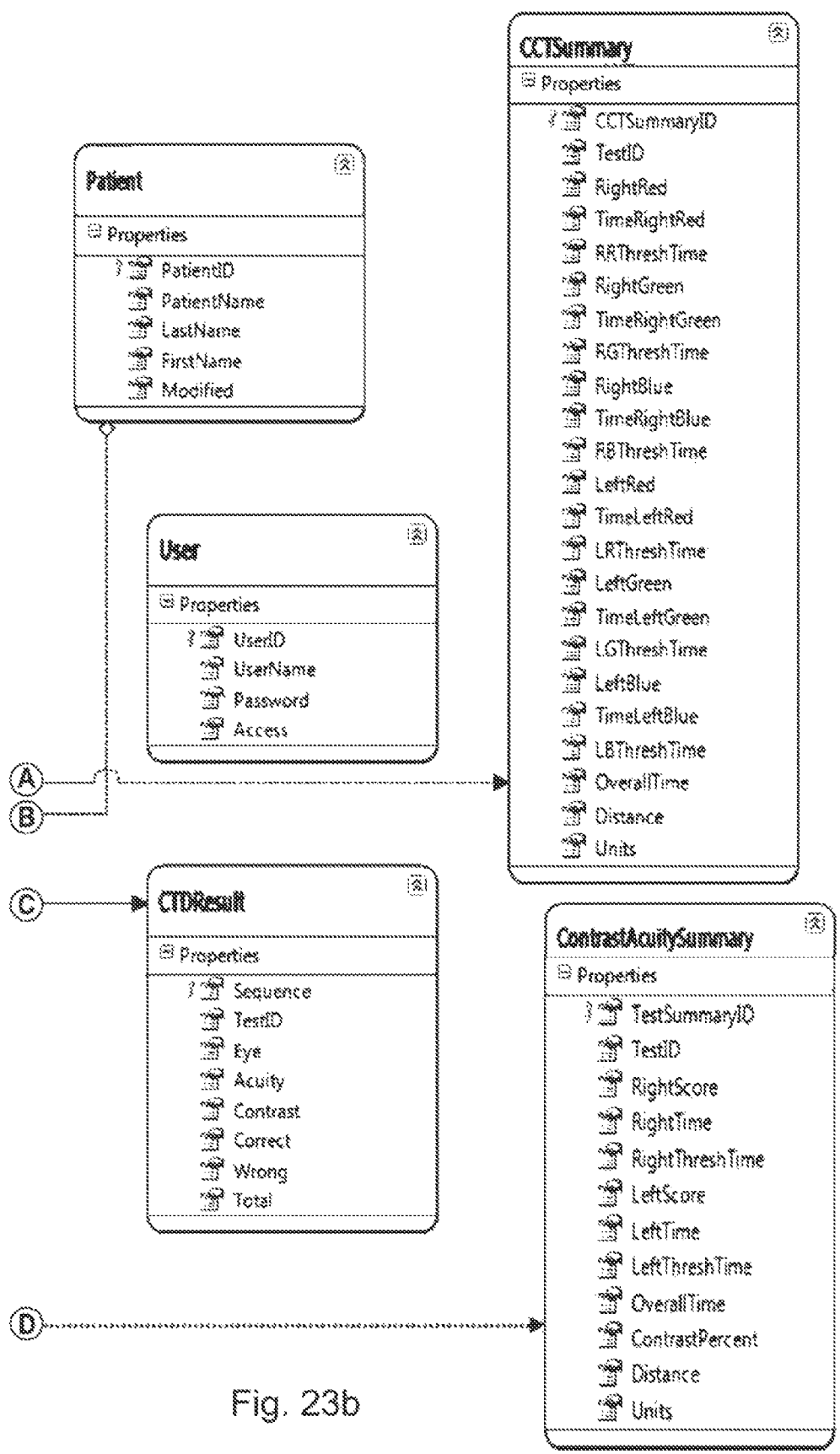
FIG. 23b is an enlarged view of the enclosed region 23b shown in FIG. 23.
Figure 24:
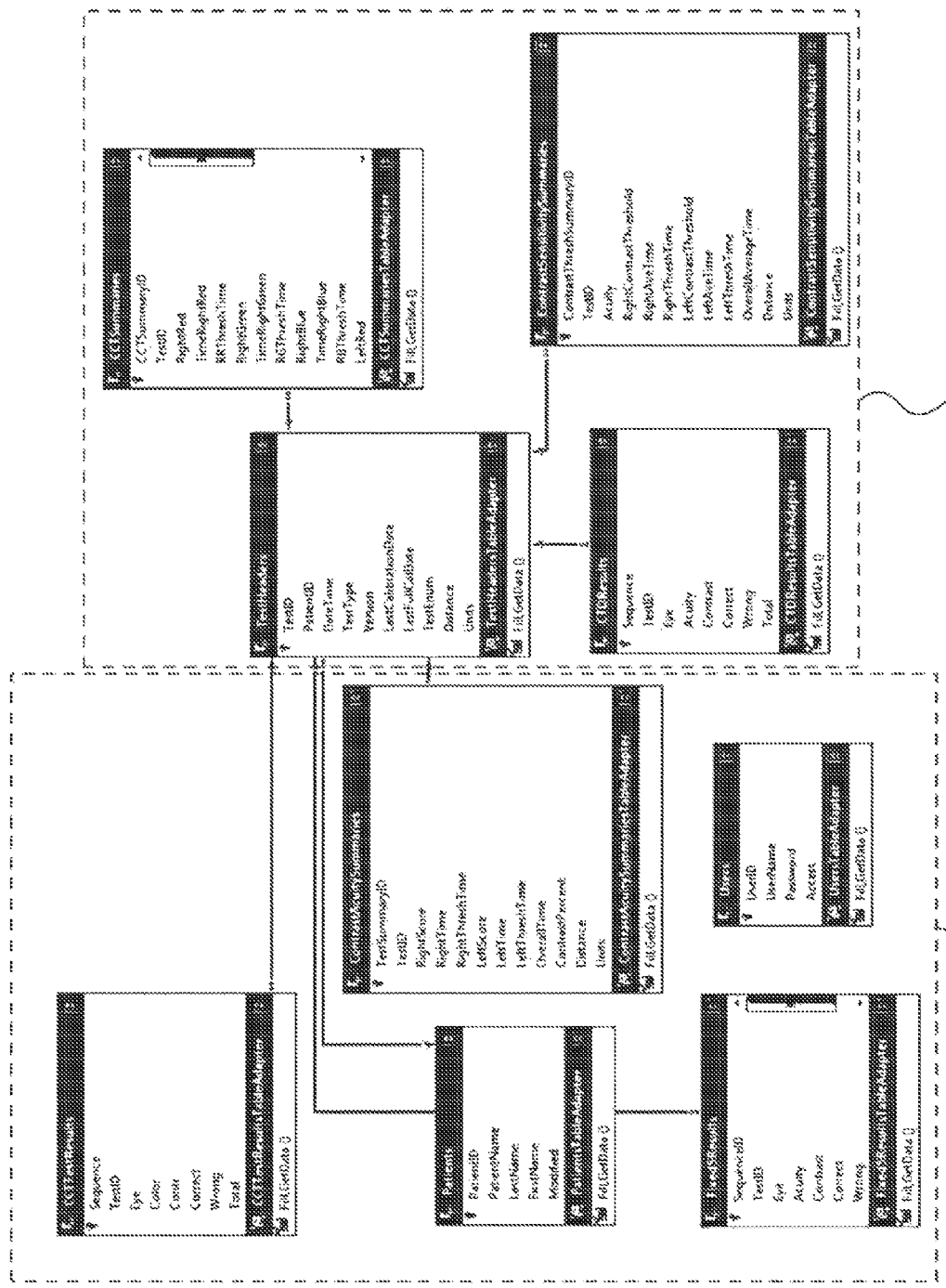
FIG. 24 is a diagram of the invention.
Figure 24A:
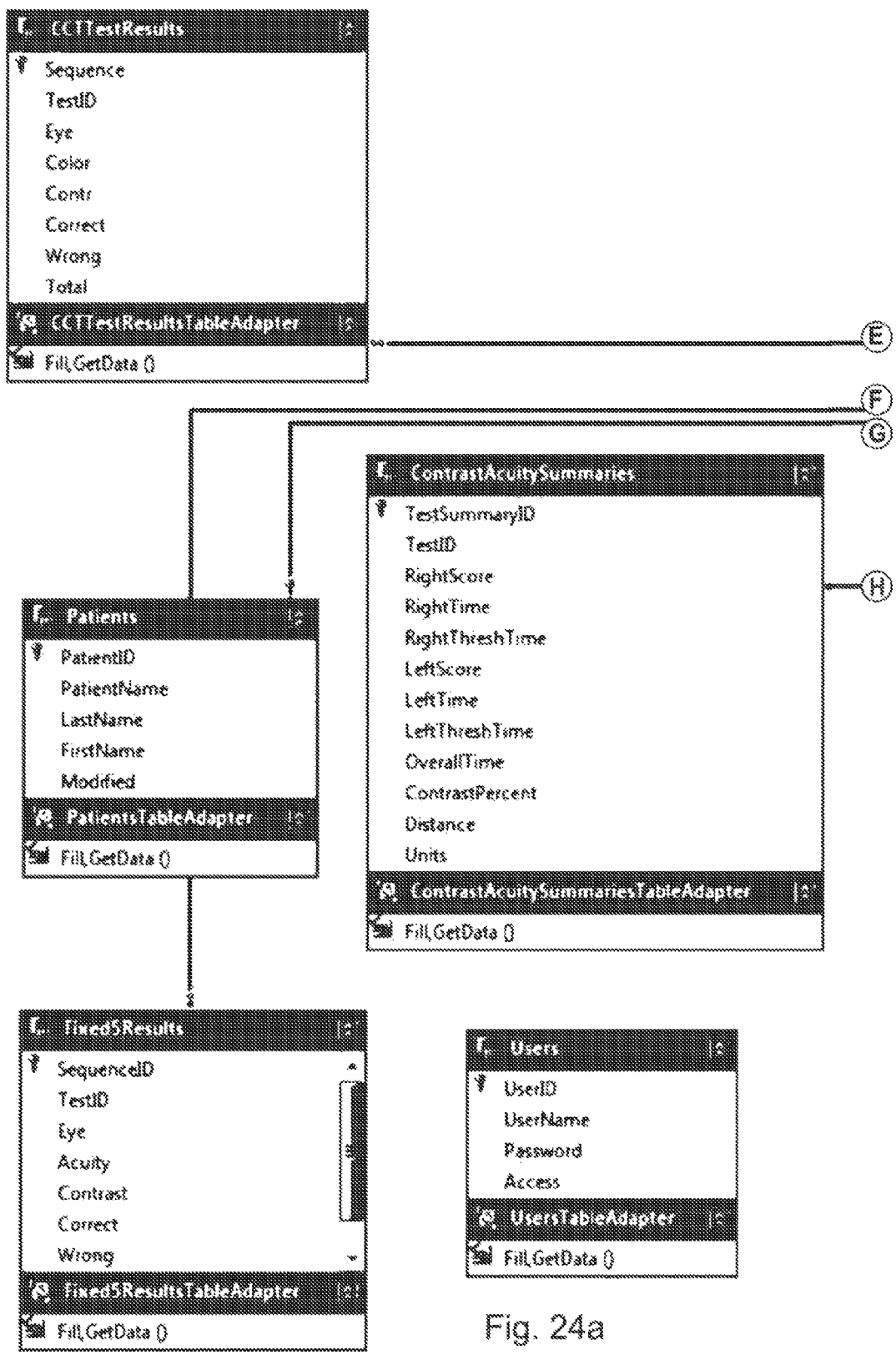
FIG. 24a is an enlarged view of the enclosed region 24a shown in FIG. 24; and,
FIG. 24b is an enlarged view of the enclosed region 24b shown in FIG. 24.
Figure 24B:
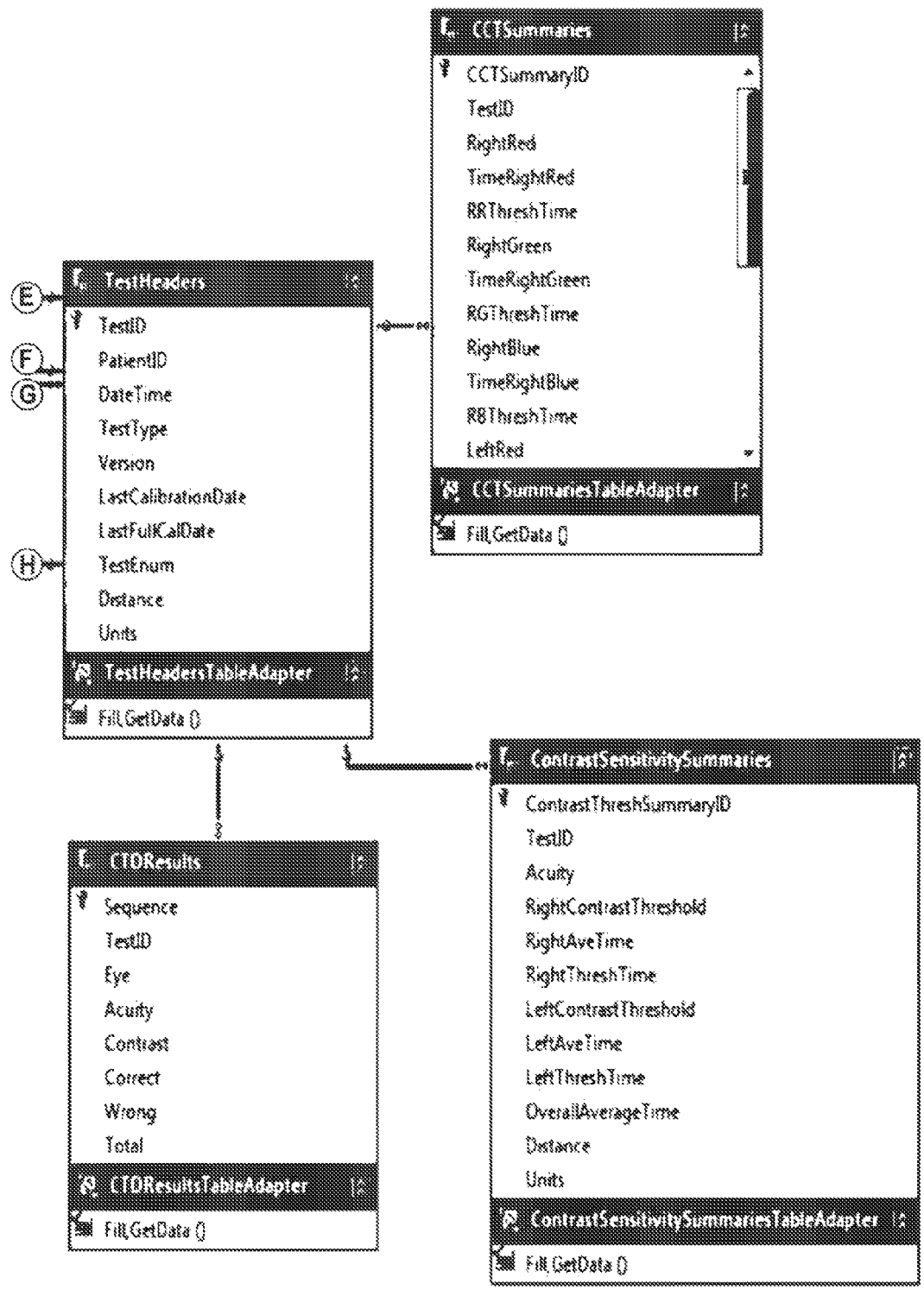

Reports are shown in FIGS. 15-18, 21-22. Significantly, CCT scores are shown in red, green and blue. Red CCT scores are shown with a single dashed line connecting circles. Green CCT scores are shown as a bar connecting squares. Blue CCT scores are shown as a double dashed line connecting triangles. The circles, squares and triangles refer to CCT scores. The lines connecting the CCT scores are generated to show trends and whether a patient's aptitude for color vision is deteriorating. Some reports include bar graphs (FIG. 16) and line graphs (FIG. 17). The colors red, yellow and green are also used to indicate color deficiency, possible deficiency, and normal vision, respectively. FIGS. 15a, 16a, 17a, and 18a show the enclosed areas 15a, 16a, 17a, and 18a, respectively, shown in FIGS. 15, 16, 17, and 18, respectively, enlarged for clarity. FIGS. 23a, 23b, 24a, and 24b show the enclosed areas 23a, 23b, 24a, and 24b, respectively, shown in FIGS. 23 and 24, respectively, enlarged for clarity.

Acquired and hereditary color deficiency can be interpreted based on a less than normal cone score in a single visit or as a drop in a specific cone score of 10 points or more from a patient's base-line. Normal color vision is indicated by a CCT score between 90-100. Possible color vision deficiency is indicated by a CCT score between 75-89. Color deficiency, hereditary or acquired, is indicated by a CCT score between 0-74. Acquired and hereditary color deficiency overlap. However, there are several characteristics that can help identify acquired vs. hereditary color deficiency. Hereditary color deficiency is indicated by selective decreases on red or green tests. Moreover, cone sensitivity scores are substantially symmetrical in the left and right eyes. In contrast, acquired color deficiency is not as selective to cone types and may show decreases on red, green and blue tests. Acquired color deficiency also usually features asymmetrical cone sensitivity scores in the left and right eyes.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A computerized method for administering a cone contrast (CCT) color vision test to a patient, comprising the steps of:
   (a) displaying a first character in a first color at a first contrast level on a display driven by said computer;
   (b) receiving a first input signal from said patient via an input device connected to said computer, where said input signal is indicative of whether said patient recognizes said first character displayed in said first color at said first contrast level;
   (c) displaying a second character in said first color at a second contrast level on said display driven by said computer;
   (d) receiving a second input signal from said patient via an input device connected to said computer, where said input signal is indicative of whether said patient recognizes said second character displayed in said first color at said second contrast level;
   (e) assigning a score to said first and second input signals, said score related to sensitivity of a cone in said patient's eye to said first color at said first and second contrast levels;
   (f) storing said score in a storage device;
   (g) comparing said score to at least one previous score associated with said patient to calculate a progression of a cone sensitivity loss in said patient; and,
   (h) displaying a graphical representation of said progression of said cone sensitivity loss in said patient.

2. The computerized method for detecting color vision loss in a patient recited in claim 1, wherein said second contrast level is lower than said first contrast level.

3. The computerized method for detecting color vision loss in a patient recited in claim 1, further comprising the step of displaying said score on a computer display.

4. The computerized method for detecting color vision loss in a patient recited in claim 1, repeating the steps of (a) through (e) of claim 1 with a second color.

5. The computerized method for detecting color vision loss in a patient recited in claim 1, repeating the steps of (a) through (e) of claim 1 with a third color.

6. The computerized method for administering a color vision test in a patient recited in claim 1, further comprising the steps of periodically verifying a calibration of said first color and said first contrast level of said first character to be displayed on said display, where said verifying is accomplished by software.

7. The computerized method for detecting color vision loss in a patient recited in claim 6, wherein the step of verifying a calibration is automatic if said calibration fails.

8. The computerized method for detecting color vision loss in a patient recited in claim 1, wherein said first color is red.

9. The computerized method for detecting color vision loss in a patient recited in claim 1, wherein said first color is green.

10. The computerized method for detecting color vision loss in a patient recited in claim 1, wherein said first color is blue.

11. The computerized method for detecting color vision loss in a patient recited in claim 1, wherein said cone is an S cone.

12. The computerized method for detecting color vision loss in a patient recited in claim 1, wherein said cone is an M cone.

13. The computerized method for detecting color vision loss in a patient recited in claim 1, wherein said cone is an L cone.

14. The computerized method for detecting color vision loss in a patient recited in claim 1, further comprising the steps of imposing a limited presentation time for steps (a) and (c).

15. The computerized method for detecting color vision loss in a patient recited in claim 1, further comprising the step of alerting said patient if said progression of said cone sensitivity loss in said patient is significant.

16. The computerized method for detecting color vision loss in a patient recited in claim 1, further comprising the step of generating reports of said score.

17. The computerized method for detecting color vision loss in a patient recited in claim 4, wherein said second color is red.

18. The computerized method for detecting color vision loss in a patient recited in claim 4, wherein said second color is green.

19. The computerized method for detecting color vision loss in a patient recited in claim 4, wherein said second color is blue.

20. The computerized method for detecting color vision loss in a patient recited in claim 5, wherein said third color is red.

21. The computerized method for detecting color vision loss in a patient recited in claim 5, wherein said third color is green.

22. The computerized method for detecting color vision loss in a patient recited in claim 5, wherein said third color is blue.

23. The computerized method for detecting color vision loss in a patient recited in claim 1, wherein said first character is a letter.

24. The computerized method for detecting color vision loss in a patient recited in claim 1, wherein said first character is a number.

25. The computerized method for detecting color vision loss in a patient recited in claim 1, wherein said first character is a symbol.

26. The computerized method for detecting color vision loss in a patient recited in claim 1, further comprising the step of differentiating said score between hereditary and acquired deficiency.

27. The computerized method for detecting color vision loss in a patient recited in claim 1, further comprising the step of differentiating said score between normal, possible deficiency, mild deficiency, moderate deficiency, and severe deficiency.

* * * * *